US008061517B2

(12) United States Patent
Loeffler et al.

(10) Patent No.: US 8,061,517 B2
(45) Date of Patent: Nov. 22, 2011

(54) HOLDING DEVICE FOR AN IMPLANT

(75) Inventors: Burkhard Loeffler, Feldberg (DE); Jens Beger, Tuttlingen (DE); Beate Celmerowski, Spaichingen (DE); Kay Fischer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 611 days.

(21) Appl. No.: 12/077,740

(22) Filed: Mar. 19, 2008

(65) Prior Publication Data

US 2008/0230423 A1 Sep. 25, 2008

(30) Foreign Application Priority Data

Mar. 22, 2007 (DE) .......................... 10 2007 015 154

(51) Int. Cl.
*B65D 85/24* (2006.01)
(52) U.S. Cl. ......... 206/339; 206/438; 206/341; 206/347
(58) Field of Classification Search .................. 206/339, 206/347, 346, 343, DIG. 820, 438, 211
See application file for complete search history.

(56) References Cited

U.S. PATENT DOCUMENTS

| 4,113,090 | A  | * | 9/1978  | Carstens ....................... 206/365 |
| 4,923,471 | A  |   | 5/1990  | Morgan |
| 5,622,024 | A  | * | 4/1997  | Habermehl .................. 52/747.1 |
| 6,802,421 | B1 | * | 10/2004 | Impellizzeri .................. 206/438 |
| 6,929,646 | B2 |   | 8/2005  | Gambale |
| 7,650,991 | B2 | * | 1/2010  | Hester et al. .................. 206/339 |
| 2006/0006087 | A1 | * | 1/2006 | Lin .............................. 206/347 |
| 2007/0095689 | A1 |   | 5/2007 | Pratt et al. |
| 2008/0302688 | A1 | * | 12/2008 | Iaconi-Forrer et al. ....... 206/339 |

FOREIGN PATENT DOCUMENTS

| DE | 690 29 245   | 5/1997  |
| DE | 202 01 202   | 11/2002 |
| DE | 699 21 864   | 10/2005 |
| FR | 2 785 033    | 4/2000  |
| WO | 99/52465     | 10/1999 |
| WO | 02/30315     | 4/2002  |
| WO | 2005/092231  | 10/2005 |
| WO | 2006/124188  | 11/2006 |
| WO | 2009/024189  | 2/2009  |

\* cited by examiner

*Primary Examiner* — J. Gregory Pickett
*Assistant Examiner* — Raven Collins
(74) *Attorney, Agent, or Firm* — Lipsitz & McAllister, LLC

(57) ABSTRACT

In order to improve a holding device for an implant, comprising a first connecting device for releasably connecting the holding device and the implant, such that very small implants, in particular, are easy to handle, it is suggested that the holding device have a second connecting device for releasably connecting the holding device and a storage unit.

31 Claims, 21 Drawing Sheets

HOLDING DEVICE FOR AN IMPLANT

The present disclosure relates to the subject matter disclosed in German patent application No. 10 2007 015 154.5 of Mar. 22, 2007, which is incorporated herein by reference in its entirety and for all purposes.

BACKGROUND OF THE INVENTION

The present invention relates to a holding device for an implant, comprising a first connecting device for releasably connecting the holding device and the implant.

The present invention also relates to a storage unit for accommodating and/or securing at least one holding device for an implant in place, wherein the holding device comprises a first connecting device for releasably connecting the holding device and the implant.

A holding device of the type described at the outset is known, for example, from U.S. Pat. No. 6,929,646 B2. This holding device has an elongated handle portion, with the aid of which an implant connected to the handle portion can be brought into a desired implanting position and location relative to a body part to be operated. After the implant has been attached to the body part, the handle portion can be separated from the implant.

It has been shown that the organization and handling of, in particular, very small implants is a problem. These implants differ from one another, at times, only very slightly but must be made available in numerous variations for a specific operation so that a surgeon can decide during the course of an operation which of the implants altogether available should be used. In some countries it is, in addition, necessary to document exactly what and how many implants have been used during the course of an operation.

It would, therefore, be desirable to make a holding device and a storage unit of the type described at the outset available, with which very small implants, in particular, are easy to handle.

SUMMARY OF THE INVENTION

In the case of a holding device of the type described at the outset, it is suggested that the holding device have a second connecting device for releasably connecting the holding device and a storage unit. The holding device therefore makes it possible, with the aid of a first connecting device, to secure an implant or several implants releasably in place on the holding device. With the aid of the second connecting device of the holding device, this can be releasably connected to a storage unit. The holding device of a further development enables a separate holding device to be made available for each implant or for a group of implants so that each implant or each group of implants can be handled more easily with the aid of the associated holding device. The holding devices may be connected to the storage unit such that the implants can be clearly arranged and can be handled together with the aid of the storage unit.

The first connecting device and the second connecting device can preferably be actuated independently of one another. As a result, an implant can be connected to the holding device with the aid of the first connecting device and be released from the holding device in that the first connecting device is actuated. This actuation is independent of whether the holding device is connected to the storage unit with the aid of the second connecting device or is released from it. In a corresponding manner, the second connecting device can be actuated in order to connect the holding device to the storage unit or release the holding device from the storage unit without this having any influence on the first connecting device and, therefore, on the connection between an implant and the holding device.

The first connecting device can preferably be transferred from a first connecting position, in which an implant can be or is connected to the holding device, into a first release position, in which the holding device releases the implant. As a result, the implant can be fixed reliably on the holding device in the first connecting position of the first connecting device and be removed from the holding device in a simple manner in the first release position of the first connecting device.

The first connecting device is preferably designed in such a manner that a first releasing force is required to transfer the first connecting device from the first connecting position into the first release position. The first releasing force defines the resistance which must be overcome for separation of the implant from the holding device. It is recommended that a releasing force be provided which is so great that an implant cannot be unintentionally detached from the holding device, for example, when the holding device is subject to slight shaking during transport. On the other hand, the first releasing force should be small enough for an implant to be releasable from the holding device manually or with the aid of a removing tool.

The holding device preferably comprises a first restoring device which transfers the first connecting device from the first release position into the first connecting position. A preferential position of the first connecting device can be defined with the aid of the first restoring device and this corresponds to the first connecting position. This preferential position can be taken up independently of whether an implant is held in the holding device or not.

It is favorable when the second connecting device can be transferred from a second connecting position, in which the holding device can be or is connected to the storage unit, into a second release position, in which the holding device can be released from the storage unit. In this way, the holding device can be secured reliably on the storage unit in the second connecting position of the second connecting device and so the holding device itself does not have to be handled but rather it can be handled with the aid of the storage unit. The holding device can be released from the storage unit in the second release position of the second connecting device so that the holding device can be handled independently of the storage unit.

The second connecting device is preferably designed in such a manner that a second releasing force is necessary to transfer the second connecting device from the second connecting position into the second release position. This second releasing force should be great enough to avoid any unintentional release of the holding device from the storage unit. The second releasing force should, on the other hand, be small enough to be able to remove the holding device from the storage unit preferably without the aid of tools.

In addition, it is preferred when the holding device comprises a second restoring device which transfers the second connecting device from the second release position into the second connecting position. A preferential position of the second connecting device can be defined with the aid of the second restoring device and this corresponds to the second connecting position. In this respect, a transfer into this preferential position can be carried out independently of whether the holding device is connected to the storage unit or not.

It is particularly preferred when the first releasing force and the second releasing force differ from one another according to amount and/or direction. As a result, any unintentional, simultaneous actuation of the first connecting device and the second connecting device can be avoided. It is, therefore, ensured that when the first releasing force is applied only the first connecting device is brought from the first connecting position into the first release position without this having any influence on the state of the second connecting device. In a corresponding manner, when the second releasing force is applied this causes a transfer of the second connecting device from the second connecting position into the second release position without this influencing the state of the first connecting device.

It is particularly preferred when the first releasing force and the second releasing force are linearly independent of one another. This makes it possible to decide, by selecting the corresponding release direction, whether the first connecting device is intended to be brought from the first connecting position into the first release position or whether the second connecting device is intended to be brought from the second connecting position into the second release position. As a result of the first and second release directions being linearly independent, it is possible to rule out that either of the two connecting devices will be brought from its connecting position into its release position in an unintentional manner. This applies irrespective of whether the first releasing force is smaller, the same as or greater than the second releasing force.

In addition, it is preferred when the first releasing force is smaller than the second releasing force. This makes it possible to adjust the releasing forces such that even when the releasing forces are intended to be oriented in the same direction the first connecting device will be brought, first of all, from the first connecting position into the first release position and then the second connecting device will be brought from the second connecting position into the second release position.

The first connecting device is preferably designed in such a manner that the implant can be handled in a first handling direction during movement from a first holding position, in which the implant is connected to the holding device, into a first release position, in which the implant is released from the holding device. With the handling direction it is possible to determine the direction, in which a surgeon must handle the implant in order to separate it from the holding device.

Furthermore, the second connecting device is preferably designed in such a manner that the holding device can be handled in a second handling direction during movement from a second holding position, in which the holding device is connected to the storage unit, into a second release position, in which the holding device is released from the storage unit. With the aid of the second handling direction it is possible to define the direction, in which the holding device must be handled in order to separate it from the storage unit.

It is particularly preferred when the first handling direction and the second handling direction are linearly independent of one another. When a surgeon releases an implant from the holding device in accordance with the first handling direction, any release of the holding device at the same time from the storage unit is precluded as a result of the linear independence of the handling directions. It is ensured in a corresponding manner that when the second handling direction is chosen to release the holding device from the storage unit an implant possibly connected to the holding device will not be released from the holding device.

It is particularly preferred when the first handling direction and the second handling direction are at right angles or essentially at right angles to one another. This makes a particularly simple handling of the implant, the holding device and the storage unit possible, with which any unintentional release of the implant from the holding device and any unintentional release of the holding device from the storage unit is precluded.

The holding device preferably defines a holding axis which predetermines the position and/or the location of the implant when it is connected to the holding device. In this way, it is possible to define an absolute spatial position and/or spatial location of an implant when the holding device is connected to a storage unit.

It is particularly preferred when the holding axis and the first handling direction are at right angles or essentially at right angles to one another. This makes a particularly simple and gentle transfer of the implant from the first holding position into the first release position possible.

It is favorable when the holding axis and the second handling direction are parallel or essentially parallel to one another. This makes a space-saving arrangement of the implant on the holding device and of the holding device on the storage unit possible.

The first connecting device preferably comprises at least one holding element which is designed to connect the implant to the holding device in the first connecting position of the first connecting device. Such a holding element can make only a one-time transfer of the first connecting device from the first connecting position into the first release position possible. Such a holding element can also make a change between the first connecting position and the first release position possible many times.

It is favorable when the at least one holding element is tongue-shaped. This makes an elastic movement of the holding element between the first connecting position and the first release position possible.

In addition or optionally, the at least one holding element can also be in the shape of a circular segment. As a result of this, implants, which have implant sections which are shaped in accordance with the circular segment shape of a holding element, may be connected to the holding device in a particularly reliable manner. A holding element in the shape of a circular segment can, in addition and where applicable, prevent any release of the implant from the holding device in a direction deviating from the first handling direction.

It is preferable when the at least one holding element can be moved and/or deformed within a holding plane. As a result of the movability and/or deformability of the at least one holding element within the holding plane, the amount of the first releasing force which is necessary for the transfer of the first connecting device from the first connecting position into the first release position can be defined in a particularly exact manner.

The holding plane is preferably at right angles or essentially at right angles to the holding axis. This makes it possible, in particular, in the case of an essentially elongated implant, for example, a bone screw to release this from the holding device in a first handling direction which is at right angles to the holding axis. As a result of this, it is possible for the implant and the holding device to be subjected to only a minimal frictional contact during transfer of the implant from the first holding position into the first release position.

It is favorable when the first connecting device has at least two holding elements. This makes it possible to introduce the first releasing force, which is required for transfer of the first connecting device from the first connecting position into the first release position, into at least two holding elements which are moved and/or deformed during the specified transfer. In this way, the mechanical load on the individual holding elements can be minimized.

The at least two holding elements can preferably be moved in opening directions opposite to one another in order to transfer the first connecting device from the first connecting position into the first release position. In this way, the first releasing force can be distributed uniformly onto the at least two holding elements.

In addition, it is preferable when the at least two holding elements can be moved in closing directions opposite to one another in order to transfer the first connecting device from the first release position into the first connecting position. This makes a gentle and self-centering transfer of the implant from the first release position into the first holding position possible.

It is particularly preferred when at least one holding element builds up a first restoring force, with which the first connecting device can be transferred back into the first connecting position, in order to form the first restoring device during transfer of the first connecting device from the first connecting position into the first release position. This can be ensured, for example, by selecting a corresponding material, for example, plastic so that the holding element is elastically deformable and can build up a first restoring force during deflection out of a basic position which corresponds to the first connecting position. As a result of this, a particularly simple construction of the first restoring device is ensured.

It is favorable when the at least one holding element limits an implant receptacle for accommodating the implant. As a result, the holding element contributes to an exact positioning of an implant on the holding device.

It is, in addition, favorable when the implant receptacle has an undercut. This makes a particularly reliable connection of the implant and the holding device possible.

It is advantageous when the implant receptacle is fully enclosed on its circumferential side. This makes a particularly reliable fixing of the implant to the holding device possible.

It is favorable when the first connecting device comprises at least one contact element which can abut on the implant in a tensioned manner in the first connecting position of the first connecting device. It is possible in a particularly simple manner with such a contact element for an implant to be secured in place on the holding device free from clearance without the first connecting device of the holding device needing to meet high tolerance requirements.

The contact segment advantageously limits the implant receptacle. As a result of this, a compact holding device can be created which makes a clearance-free connection of the holding device and implant possible.

It is advantageous when the at least one contact element is in the shape of a circular segment. Such a contact element may abut on a curved implant section particularly well, providing contact over a large surface area.

It is particularly preferred when the holding device has an indicating device which indicates an at least one-time transfer of the first connecting device from the first connecting position into the first release position. Such an indicating device makes it possible to ascertain without any doubt that an implant was connected to the holding device and has been released from the holding device. It can be concluded from this that this implant has been used during the course of an operation. This implant can be allocated with the aid of that holding device, the indicating device of which indicates the transfer of the first connecting device from the first connecting position into the first release position. It is understood that the indicating device described can also be provided in the case of holding devices which have only a first connecting device for releasably connecting the holding device and an implant and no second connecting device for releasably connecting the holding device and a storage unit.

The indicating device preferably comprises at least one indicating element which can be destroyed and/or plastically deformed during transfer of the first connecting device from the first connecting position into the first release position. This makes a particularly simple configuration of the indicating device possible.

It is preferred when the indicating device has at least one connecting section for the connection of at least two indicating elements and/or for the connection of the at least one indicating element to an additional part of the holding device, wherein the connecting section can be severed during transfer of the first connecting device from the first connecting position into the first release position. This makes a particularly simple construction of the indicating device possible. The connecting section can comprise, in particular, a predetermined breaking point or be formed by a predetermined breaking point.

It is favorable when the at least one indicating element is of a tape-like shape. This makes destruction and/or plastic deformation of the indicating element possible with the aid of relatively small destruction and/or deforming forces.

It is advantageous when the at least one indicating element has element sections which are movable relative to one another and extend in planes angled in relation to one another. In this way, the triggering force required for triggering the indicating device can be adjusted particularly well.

The at least one indicating element is favorably formed by a holding element. This makes a particularly simple construction of the holding device possible. In addition, it is ensured in a particularly reliable manner that the indicating device is also triggered when the first releasing force is applied in order to transfer the first connecting device from the first connecting position into the first release position.

It is favorable when the holding device comprises a plate-like basic member. The basic member makes a particularly compact configuration of the holding device possible.

It is preferred when the basic member extends in the holding plane. This makes a space-saving arrangement of the holding elements on the basic member possible.

In addition, it is preferred when the basic member extends at right angles or essentially at right angles to the holding axis. This makes a space-saving arrangement of an implant on the holding device possible as well as a space-saving arrangement of the holding device on the storage unit.

It is favorable when the at least one holding element and/or the at least one contact element and/or the at least one indicating element is or are arranged on the basic member. As a result of this, a particularly compact holding device can be created.

The at least one holding element and/or the at least one contact element and/or the at least one indicating element is or are preferably designed in one piece with the basic member. This makes a particularly inexpensive production of the holding device possible.

The holding device preferably comprises a data storage device for storing implant data. This makes a clear allocation of an implant connectable to the holding device and of the holding device possible. The implant data can relate, for example, to a producer, an article number, a batch number and/or to other properties of the implant. By reading the data storage device it is possible to be able to trace the implant data even when the implant has already been detached from the holding device. This makes it easier to trace which implant has been used during the course of an operation.

It is favorable when the data storage device is connected non-detachably to the holding device. This makes the allocation of the implant data to an implant connected to the holding device or detached from the holding device easier.

It is advantageous when the data storage device is writable several times. This makes it possible for the holding device to be used for different implants or for a group of different implants.

It is particularly preferred when the data storage device is designed to display the implant data in the form of an optical data storage device. This makes an optical identification of very small implants, in particular, possible which have, where applicable, no surface area which is large enough to display implant data.

It is favorable when the implant data are present in an alphanumeric form, as a barcode and/or as a matrix code. As a result, the implant data can be read directly without the aid of additional devices and/or can be detected easily, for example, with the aid of a scanner.

It is particularly preferred when the data storage device comprises a visible surface for the display of the implant data. This makes simple reading or scanning of the implant data possible.

It is particularly preferred when the visible surface is formed on the basic member and so the construction of the holding device is simplified further.

It is favorable when the implant data are designed to be in one piece with the holding device. As a result of this, a data storage device need not be made available separately. When the holding device is produced, for example, in an injection molding process, the implant data can be provided during the same production procedure as a result of corresponding configuration of the injection mold.

It is advantageous when the data storage device is designed in the form of an electronic data storage device. Such a data storage device makes it possible to store very extensive implant data, as well.

It is favorable when the data storage device comprises at least one RFID element. Such an element may be integrated inexpensively into the holding device or arranged on it, for example, by way of injection into a plastic material. In addition, an RFID element can be read without contact with the aid of a suitable reading device for reading the implant data.

It is favorable when the second connecting device comprises at least one connecting element which is designed to connect the holding device to the storage unit in the second connecting position of the second connecting device. The holding device can be connected reliably to the storage unit and easily detached from the storage unit with the aid of the at least one connecting element.

It is particularly preferred when the at least one connecting element comprises at least one snap-in element for forming a snap-in connection or is designed as a snap-in element, wherein the snap-in element is or can be brought into engagement interlockingly with the storage unit in the second connecting position of the second connecting device. Such a snap-in element makes a particularly reliable connection of the holding device and the storage unit possible. In addition, the transfer of the second connecting device from the second release position into the second connecting position can take place at the same time as a corresponding snap-in procedure of the snap-in element, whereby a good acoustic and/or optical indication conveys to an operator the fact that the second connecting device has reached its second connecting position.

The at least one connecting element can preferably be moved and/or deformed within a plane of connection. In this way, a second releasing force, which is possibly required for transfer of the second connecting device from the second connecting position into the second release position, can be defined exactly with respect to amount and/or direction.

The plane of connection is preferably parallel or essentially parallel to the holding axis of the implant. This makes a particularly simple construction of the second connecting device possible.

In addition, it is advantageous when the second connecting device has at least two connecting elements. As a result of this, the second releasing force, which is possibly required for transfer of the second connecting device from the second connecting position into the second release position, can be introduced into several connecting elements and so the mechanical load on the individual connecting elements is minimized.

The at least two connecting elements can preferably be moved in opening directions opposite to one another in order to transfer the second connecting device from the second connecting position into the second release position. This makes a comfortable handling of the holding device possible during the transfer of the second connecting device from the second connecting position into the second release position.

Furthermore, the at least two connecting elements can preferably be moved in closing directions opposite to one another in order to transfer the second connecting device from the second release position into the second connecting position. This makes a comfortable handling of the holding device possible during the transfer of the second connecting device from the second release position into the second connecting position.

It is favorable when the at least one connecting element builds up a second restoring force, with which the second connecting device can be transferred back into the second connecting position, for forming the second restoring device during transfer of the second connecting device from the second connecting position into the second release position. This makes a particularly simple construction of the second restoring device possible and this has the effect that the second connecting position of the second connecting device is the preferential position of the second connecting device.

The at least one connecting element preferably limits an undercut area for the accommodation of a section of the storage unit in the second connecting position of the second connecting device. As a result of this, a particularly reliable connection between the holding device and the storage unit is ensured.

It is preferred when the undercut area is limited by a contact surface of the basic member. In this way, an additional function associated with the second connecting device can be realized with the aid of the basic member.

It is advantageous when the second connecting device comprises at least one essentially U-shaped material section which has two legs of the U which extend parallel or essentially parallel to the holding axis and are connected to one another via a base of the U. Such a material section makes a simple arrangement and/or realization of at least one connecting element possible.

The holding axis is favorably arranged between two legs of the U. In this way, the implant can be protected from mechanical influences with the aid of the legs of the U when the implant is connected to the holding device.

Furthermore, it can be advantageous when the holding axis is arranged outside a space formed between the legs of the U. This makes a particularly compact construction of the second connecting device possible.

The second connecting device preferably comprises at least one actuating element for transferring the second connecting device from the second connecting position into the second release position. As a result of this, the holding device can be detached from the storage unit in a particularly simple manner.

The at least one actuating element is preferably designed in the form of a gripping section. As a result of this, the second connecting device can be actuated manually.

The at least one actuating element is arranged in an advantageous manner at a free end of a leg of the U. This makes a particularly simple transfer of the second connecting device from the second connecting position into the second release position possible.

Furthermore, the at least one actuating element is preferably arranged on the basic member. As a result of this, the handling of the holding device is made easier.

It is particularly preferred when at least one actuating element and at least one connecting element of the second connecting device are arranged on oppositely located sides of the basic member when looking along the holding axis of the implant. As a result of this, the second connecting device can be arranged relative to the storage unit in a space in the storage unit which is comparatively difficult to access but is well protected whereas the actuating element can be arranged on the oppositely located side of the basic member so as to be easily accessible.

The holding device preferably comprises at least one securing device which prevents any implantation of the implant when the implant is connected to the holding device. This has the advantage that an implant which is connected to the holding device cannot be used unintentionally together with the holding device during the course of an operation on a body part to be operated.

It is particularly favorable when the securing device comprises at least one securing section spaced from the holding axis. This makes it possible to protect a functional area of the implant, for example, a threaded section with the aid of the securing section so that this functional area cannot be brought into engagement with a body part to be operated.

The securing section is preferably arranged at an angle relative to the basic member, in particular, at right angles or essentially at right angles. This makes a particularly compact construction of the holding device possible. It is, in addition, favorable when the securing section is essentially C-shaped in a cross section at right angles to the holding axis. This allows a functional area of an implant to be protected over a particularly large surface area. In addition, the securing device allows an extensive mechanical protection of the implant.

In cross sections at right angles to the holding axis, the securing section is preferably larger in an area adjacent to the basic member than in an area removed from the basic member. This makes a particularly simple positioning of the holding device on the storage unit possible. In this respect, the holding device can be brought closer to the storage unit, first of all, with its area removed from the basic member and then be brought into abutment on the storage unit with the area adjacent to the basic member.

The securing section is favorably formed by the U-shaped material section of the second connecting device. As a result of this, it is possible to dispense with a separate securing section. With the aid of the base of the U of this material section, an implant connected to the holding device can also be protected against mechanical influences in a direction parallel to the holding axis.

It is favorable when the holding device has a guiding device, with which the holding device can be positioned relative to the storage unit. This makes the handling of the holding device easier when the holding device is connected to the storage unit.

It is favorable when the guiding device has at least one guiding section which is designed to abut on a section of the storage unit. The guiding section can be formed by parts of the holding device which have already been described, for example, by parts of the second connecting device and/or by a securing section of the securing device. The guiding device can, however, also have in addition or optionally at least one separate guiding section.

When the holding device comprises at least one implant, a structural module can be made available which can be connected to a storage unit. This structural module can be made available for an operation and sterilized again when not used and made available for the next operation.

Furthermore, it is suggested for a storage unit of the type described at the outset that the holding device have a second connecting device for releasably connecting the holding device and the storage unit. The storage unit makes the handling of at least one holding device easier and, therefore, also the handling of a very small implant, in particular, which is possibly connected to the holding device. It is particularly advantageous when the storage unit allows accommodation and/or securing in place of several holding devices.

It is preferred when the storage unit is designed for an orientation of at least two holding devices identical to one another. In this way, it is easier to find a specific holding device and, therefore, a specific implant.

Furthermore, it is preferred when the storage unit is designed for an orderly arrangement of at least three holding devices. This also makes it easier to find specific holding devices and specific implants.

A particularly neat arrangement of the holding device is achieved when the storage unit is designed for an arrangement of the holding devices in rows or columns. This makes a space-saving arrangement of several holding devices on the storage unit possible, in addition.

It is favorable when the storage unit comprises at least one receptacle for accommodating and/or securing at least one holding device in place. The relative position and/or location of the holding device relative to the storage unit can be defined with the aid of the receptacle.

It is particularly preferred when the at least one holding device can be inserted into the at least one receptacle at least in sections. As a result of this, the holding devices can be arranged on the storage unit in a space-saving manner and reliably connected to it.

The storage unit preferably comprises a plate for forming or for the arrangement of the at least one receptacle. This makes an inexpensive production of the storage unit possible which can, in addition, be cleaned particularly well.

The at least one receptacle is preferably limited by a section of the plate which can be connected to the second connecting device of the holding device. As a result of this, a storage unit which is constructed in a particularly simple manner can be created.

It is favorable when the receptacle has a cross section which predetermines the rotary position of a holding device about its holding axis relative to the storage unit. In this way, the rotary position of the holding device can be predetermined and so the ease, with which this holding device and, therefore, a specific implant can be found, is improved.

It is particularly favorable when the at least one receptacle has a cross section in the form of an elongated hole. As a result of this, a preferential orientation of the holding device relative to the storage unit can be predetermined in a simple manner.

It is advantageous when the receptacle has at least one storage element projecting from the plate for connecting the storage unit to the second connecting device of a holding device. A particularly reliable connection between the holding device and the storage unit can be provided with the aid of such a storage element.

It is favorable when the storage unit has at least one spacer device which spaces the plate in relation to a mounting surface for the storage unit. This makes it possible to create a distance between the plate and the mounting surface, in which at least sections of the holding devices and/or the implants can be arranged without them coming into contact with the mounting surface.

It is preferred when the spacer device comprises a frame extending along the edge of the plate at least in sections. As a result of this, the storage unit can be placed on the mounting surface in a manner particularly secure against any tilting. When the frame extends along the entire edge of the plate, a space extending between the plate of the storage unit and the mounting surface, in which holding devices can be arranged at least in sections, is protected particularly well from mechanical influences.

A structural module consisting of a storage unit with at least one holding device makes it possible for holding devices and/or implants required for a specific operation to be made available in an orderly manner and without additional preparation steps. This structural module can be replenished after an operation, sterilized and made available for a subsequent operation.

The following description of preferred embodiments of the invention serves to explain the invention in greater detail in conjunction with the drawings.

BRIEF DESCRIPTION OF THE DRAWINGS

These show.

DETAILED DESCRIPTION OF THE INVENTION

Figure 1:
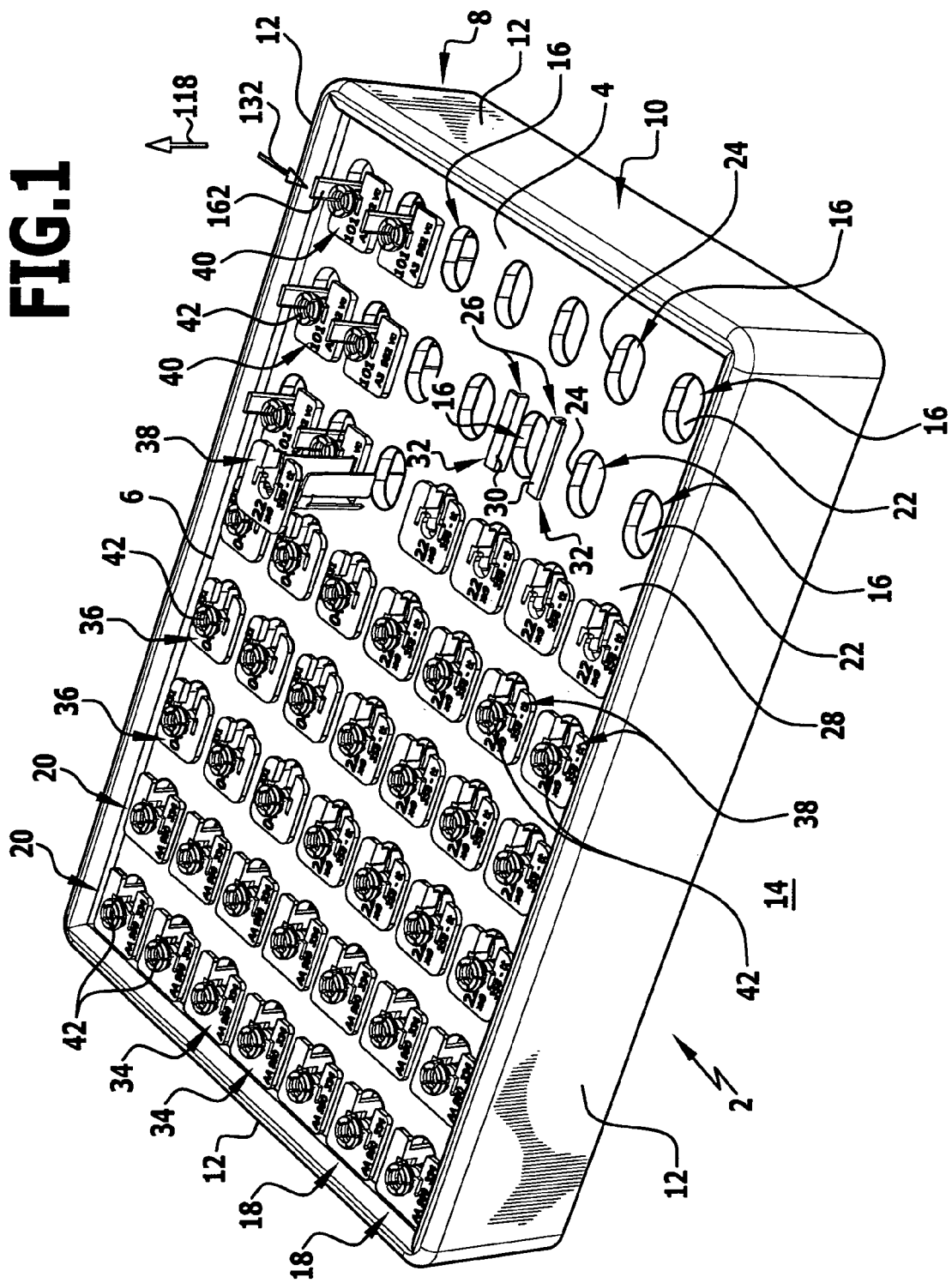
FIG. 1: a perspective view of a storage unit and a plurality of holding devices which are connected to the storage unit or released from it as well as a plurality of implants which are each connected to a holding device.

The same or functionally equivalent elements are designated in all the Figures with the same reference numerals.

In FIG. 1, a storage unit which is designed for the arrangement of holding devices for implants is designated altogether with the reference numeral 2. It has a rectangular plate 4, the plate thickness of which is a few millimeters. A spacer device designated altogether with the reference numeral 8 extends along the edge 6 of the plate 4. The spacer device is designed in the form of a frame 10 which comprises four walls 12 arranged in respective pairs at right angles to one another and connected to one another. The walls 12 extend at right angles to the plate 4 and space this from a mounting surface 14, on which the storage unit 2 is placed.

The plate 4 has a plurality of receptacles 16 which are each formed by openings provided in the plate 4. The receptacles 16 are distributed over the plate 4 in a regular manner and arranged in rows 18 which are parallel to one another and columns 20 at right angles thereto. The receptacles 16 are each designed in the form of an elongated hole, wherein the longer cross-sectional axis (without any reference numeral) extends in the direction of the rows 18 and the shorter cross-sectional axis (without any reference numeral) in the direction of the columns 20.

The plate 4 has altogether 56 receptacles 16 arranged in seven rows 18 and eight columns 20. The cross sections 22 of the receptacles 16 are of the same size and oriented identically to one another. Each receptacle 16 is limited by sections 24 of the plate 4. More details concerning the function of the sections 24 will be explained further on.

One of the receptacles 16 illustrated in FIG. 1 comprises two elongated storage elements 26. They project from an upper side 28 of the plate 4 and extend in the direction of the rows 18. The storage elements 26 comprise two storage sections 30 which are spaced from the upper side 28, extend parallel to the plate 4 and limit storage areas 32 extending in the direction of the rows 18 together with the upper side 28 of the plate 4. The function of the storage areas 32 will also be explained in detail further on.

The storage unit 2 serves to accommodate and/or secure in place a plurality of holding devices which can be releasably connected to the receptacles 16 of the plate 4. In FIG. 1, various holding devices are illustrated which are releasably connected to the storage unit 2, namely holding devices 34 (cf. FIGS. 4 and 5), holding devices 36 (cf. FIGS. 6 and 7), holding devices 38 (cf. FIGS. 8 and 9) and holding devices 40 (cf. FIGS. 10 and 11). In FIG. 1, one of the holding devices 38 is illustrated in its state detached from the storage unit 2.

Each of the holding devices 34, 36, 38, 40 serves for the arrangement of an implant 42 designed in the form of a screw. Each implant 42 can, as illustrated in FIG. 1, be releasably connected to one of the holding devices 34, 36, 38, 40.

The holding device 34 comprises a first connecting device 44 for releasably connecting the holding device 34 and an implant 42 as well as a second connecting device 46 for releasably connecting the holding device 34 and the storage unit 2.

Figure 4:
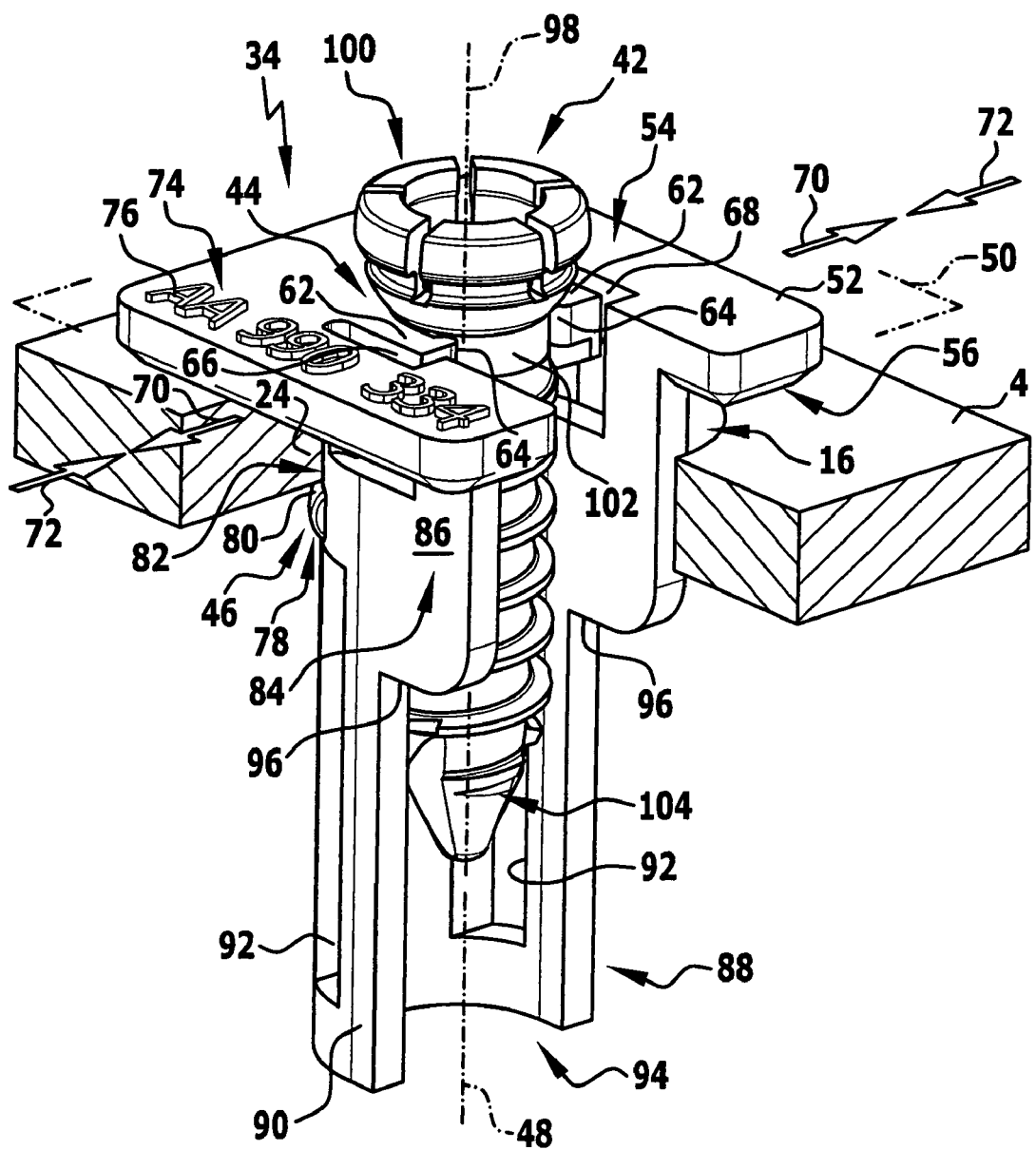
FIG. 4: a perspective view of the parts illustrated in FIG. 3, wherein the implant is releasably connected to the holding device, wherein the holding device is releasably connected to the storage unit.

The holding device 34 defines a holding axis 48, along which an implant 42 can be arranged when the implant 42 is connected to the holding device 34 and takes up a holding position (cf. FIG. 4). This position of the implant 42 will be designated in the following as first holding position.

A holding plane 50, in which an approximately square, plate-like basic member 52 extends, runs at right angles to the holding axis 48. This basic member has a visible surface 54 on the side located opposite the second connecting device 46. The basic member 52 has a contact surface 56 on its side located opposite the visible surface 54.

The first connecting device 44 comprises an implant receptacle 58 which extends in the area of the holding axis 48 at the height of the holding plane 50. The implant receptacle 58 is limited by a contact section 60 which is approximately semi-cylindrical and is formed by the basic member 52. The contact section 60 is adjoined by two holding elements 62 which are tongue-shaped and arranged so as to be located opposite one another. They have at their free ends snap-in projections 64 which face one another. The snap-in projections 64 limit the implant receptacle 58 in such a manner that an undercut results.

The basic member 52 has elongated spaces 66 and 68, respectively, on the sides of the respective holding elements 62 facing away from the implant receptacle 58. The spaces 66 and 68 have the effect that the holding elements 62 may be moved elastically in the holding plane 50. The holding elements 62 can be moved in an opening direction 70 into the respective spaces 66 and 68. The holding elements 62 can also each be moved in the direction towards the implant receptacle 58 in closing directions 72 which point towards one another.

Figure 2:
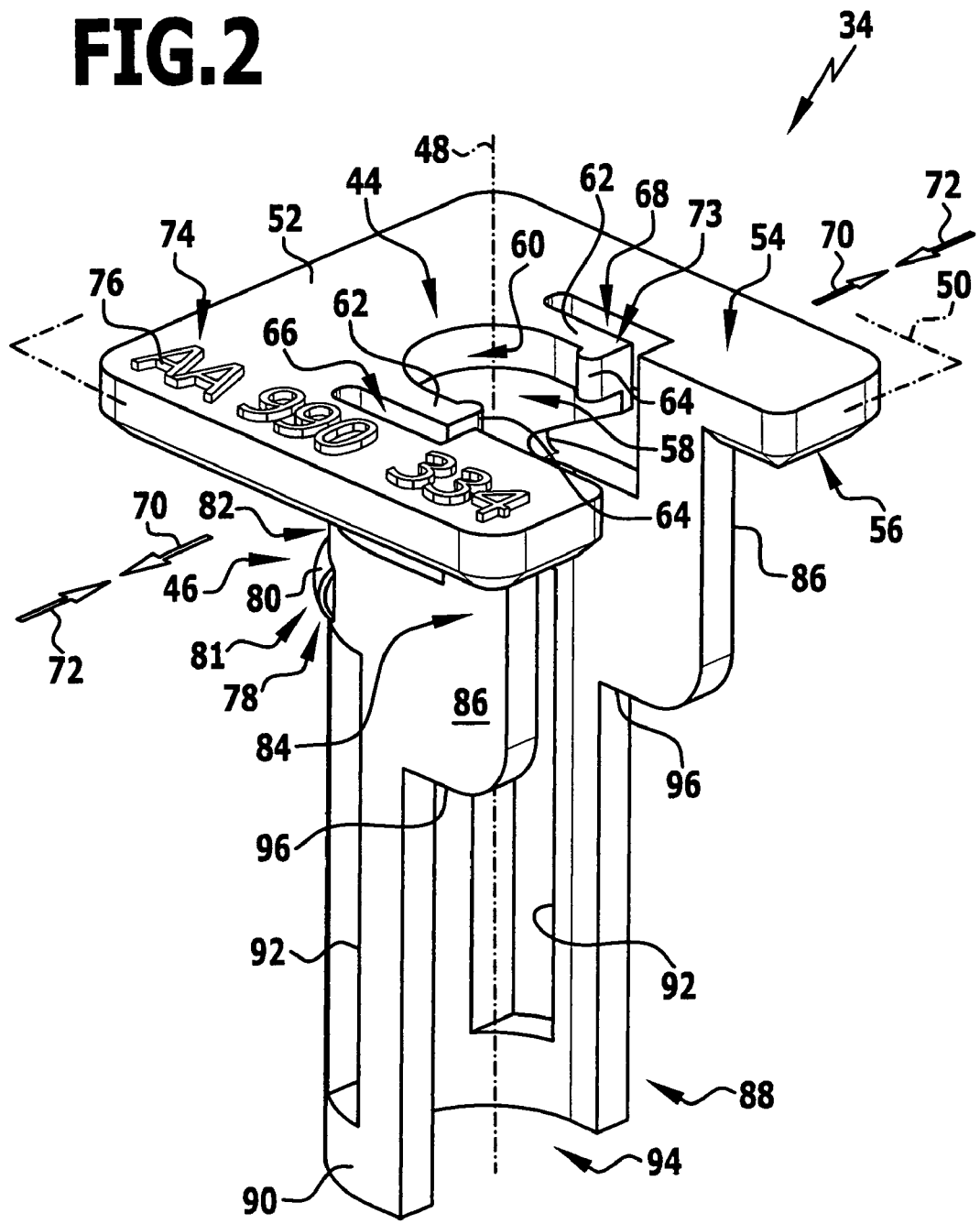
FIG. 2: a perspective view of a holding device according to a first embodiment.

The holding elements 62 are illustrated in FIG. 2 in a first connecting position of the first connecting device 44. When the holding elements 62 are deflected out of this first connecting position into the spaces 66 and 68 as a result of a first releasing force being applied, the first connecting device 44 can be transferred into a first release position. During such a transfer of the first connecting device 44 from the first connecting position into the first release position, the holding elements 62 are elastically deformed and deflected into the spaces 66 and 68. As a result of this, the holding elements 62 each build up a first restoring force which is directed towards the implant receptacle 58. The first restoring forces have the effect that the holding elements return to the position illustrated in FIG. 2 of their own accord following deflection into the spaces 66 and 68. In this way, the holding elements 62 form a first restoring device 73.

The basic member 52 comprises a data storage device designated altogether with the reference numeral 74. In the case of the holding device 34, the data storage device 74 comprises the visible surface 54 of the basic member 52. On the visible surface 52, implant data 76 are arranged which are raised above the visible surface 52 and serve to identify an implant 42 which can be connected to the holding device 34 via the first connecting device 44. The implant data 76 are alphanumeric.

Figure 3:
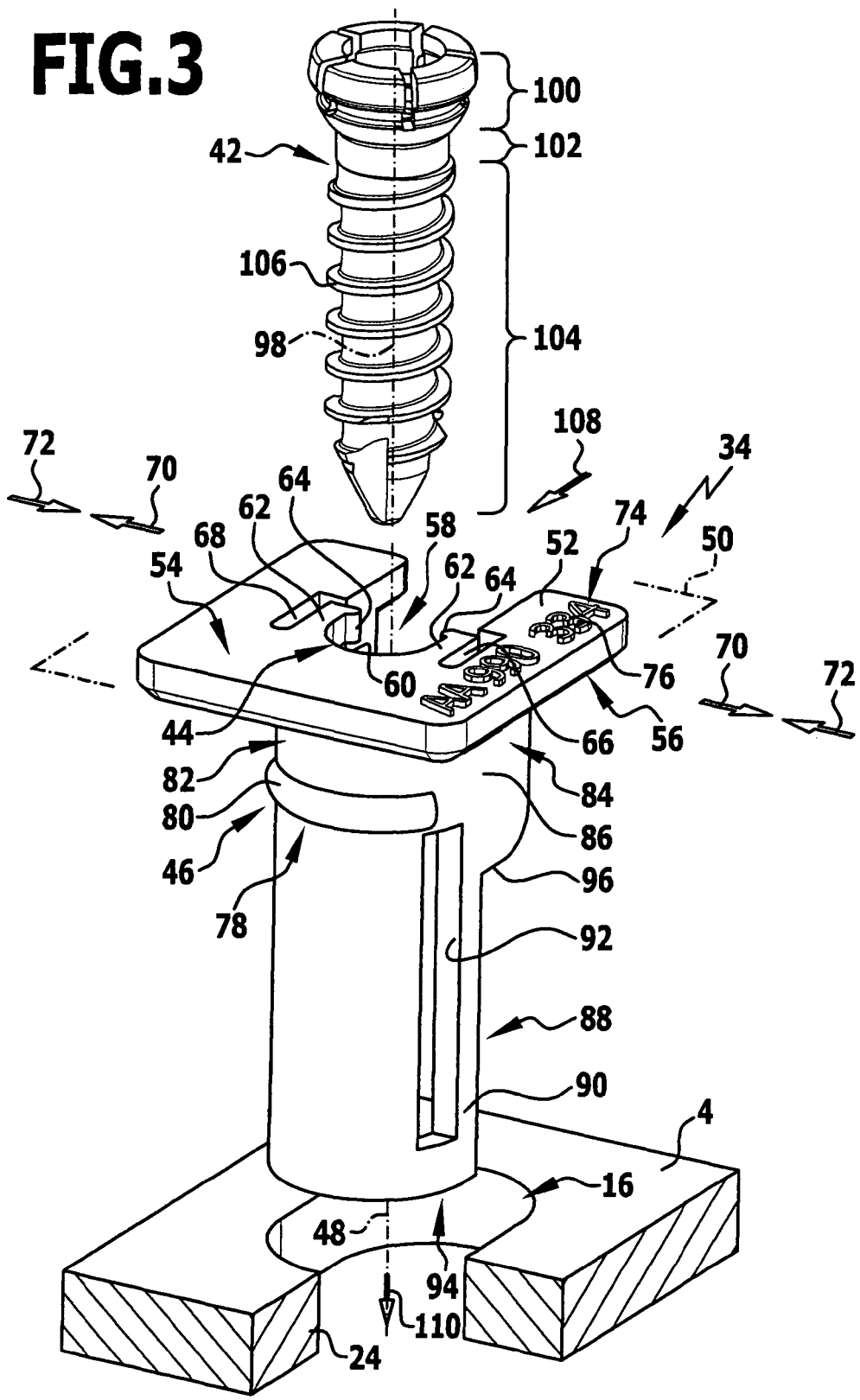
FIG. 3: an exploded view of the holding device according to FIG. 2, an implant as well as a section of the storage unit according to FIG. 1.

The second connecting device 46, with which the holding device 34 can be connected to the storage unit 2, comprises a connecting element 78 in the form of a curved snap-in element 80. Together with the contact surface 56 of the basic member 52, the snap-in element 80 limits an undercut area 82, in which a section 24 of the plate 4 of the storage unit 2, which is also illustrated in FIGS. 1, 3 and 4, can be arranged.

The connecting element 78 is illustrated in FIG. 2 in a second connecting position of the second connecting device 46. When the connecting element 78 is deformed out of this second connecting position in the direction towards the holding axis 48 as a result of a second releasing force being applied, the first connecting device 44 can be transferred into a second release position. During such a transfer of the second connecting device 46 from the second connecting position into the second release position, the connecting element 78 is elastically deformed. As a result of this, the connecting element 78 builds up a second restoring force which is directed away from the holding axis 48. This second restoring force has the effect that the connecting element 78 returns back to the position illustrated in FIG. 2 of its own accord following its deformation in the direction towards the holding axis 48. In this way, the connecting element 78 forms a second restoring device 81.

The holding device 34 comprises a guiding device 84 which has two flat guiding sections 86 which extend parallel to the holding axis 48. The guiding sections 86 serve to position the holding device 34 relative to a receptacle 16 of the storage unit 2.

The holding device 34 comprises, in addition, a securing device 88 which comprises a securing section 90 which is C-shaped in cross sections at right angles to the holding axis 48. The securing section 90 has two slits 92 which extend parallel to the holding axis 48 and are approximately rectangular. The securing section 90 has, in addition, a free end 94 on its side facing away from the basic member 52. The cross sections of the securing section 90 at right angles to the holding axis increase in size from this free end, when seen in the direction of the holding axis 48, as far as the level of two steps 96. As a result of this, the cross section of the securing device 88 is greater in an area adjacent to the basic member 52 than in an area at a distance from the basic member 52.

In FIG. 3, the holding device 34 is illustrated with an implant 42. The implant 42 is in a position released from the holding device 34.

The implant 42 extends along an implant axis 98. It has a first implant section 100 in the form of a screw head. This is adjoined by a short cylindrical implant section 102. Finally, the implant 42 has an implant section 104 which is provided with an external thread 106. The implant 42 can be secured to a body part to be operated with the aid of the external thread 106.

In order to connect the implant 42 to the holding device 34, the implant section 102 of the implant 42 can be positioned at the level of the holding plane 50 to the side in relation to the holding device 34. This position of the implant 42 is designated in the following as first release position. The implant 42 can be moved from this position into the implant receptacle 58 within the holding plane 50 in a connecting direction which is designated as 108 and is at right angles to the holding axis 48. In this respect, the holding elements 62 are moved away from one another by the implant section 102 in opening directions 70 opposite to one another until the snap-in projections 64 engage interlockingly around the implant section 102 (cf. FIG. 4).

When the implant 42 takes up its first holding position on the holding device 34, which is illustrated in FIG. 4, the implant section 100 extends beyond the visible surface 54 of the basic member 52. The implant section 102 is held in the implant receptacle 58. The implant section 104 is surrounded by the securing section 90 C-shaped in cross section at right angles to the holding axis 48.

The holding device 34 can be brought from a second release position illustrated in FIG. 3 into a position illustrated in FIG. 4, in which the holding device 34 is connected to the storage unit 2. This position of the holding device 34 is designated in the following as second holding position.

In order to bring the holding device 34 into the second holding position proceeding from the second release position, the free end 94 of the securing section 90 of the holding device 34 can be introduced into one of the receptacles 16 of the plate 4 of the storage unit 2. In this respect, the holding device 34 is moved in a connecting direction designated in FIG. 3 with the reference numeral 110 until the snap-in element 80 engages interlockingly behind the section 24 of the plate 4 and the contact surface 56 of the basic member 52 abuts on the upper side 28 of the plate 4 (cf. FIG. 4).

In FIG. 4, the first connecting device 44 is in the first connecting position. The implant 42 is connected to the holding device 34 and is in the first holding position.

In FIG. 4, the second connecting device 46 is in the second connecting position. The holding device 34 is connected to the storage unit 2 and is in the second holding position.

The arrangement illustrated in FIG. 4 makes it easy for a surgeon to handle the implant 42 since it is connected to the holding device 34 and this is, on the other hand, connected to the storage unit 2. In this respect, the implant 42 can be identified clearly with the aid of the data storage device 74.

Figure 5:
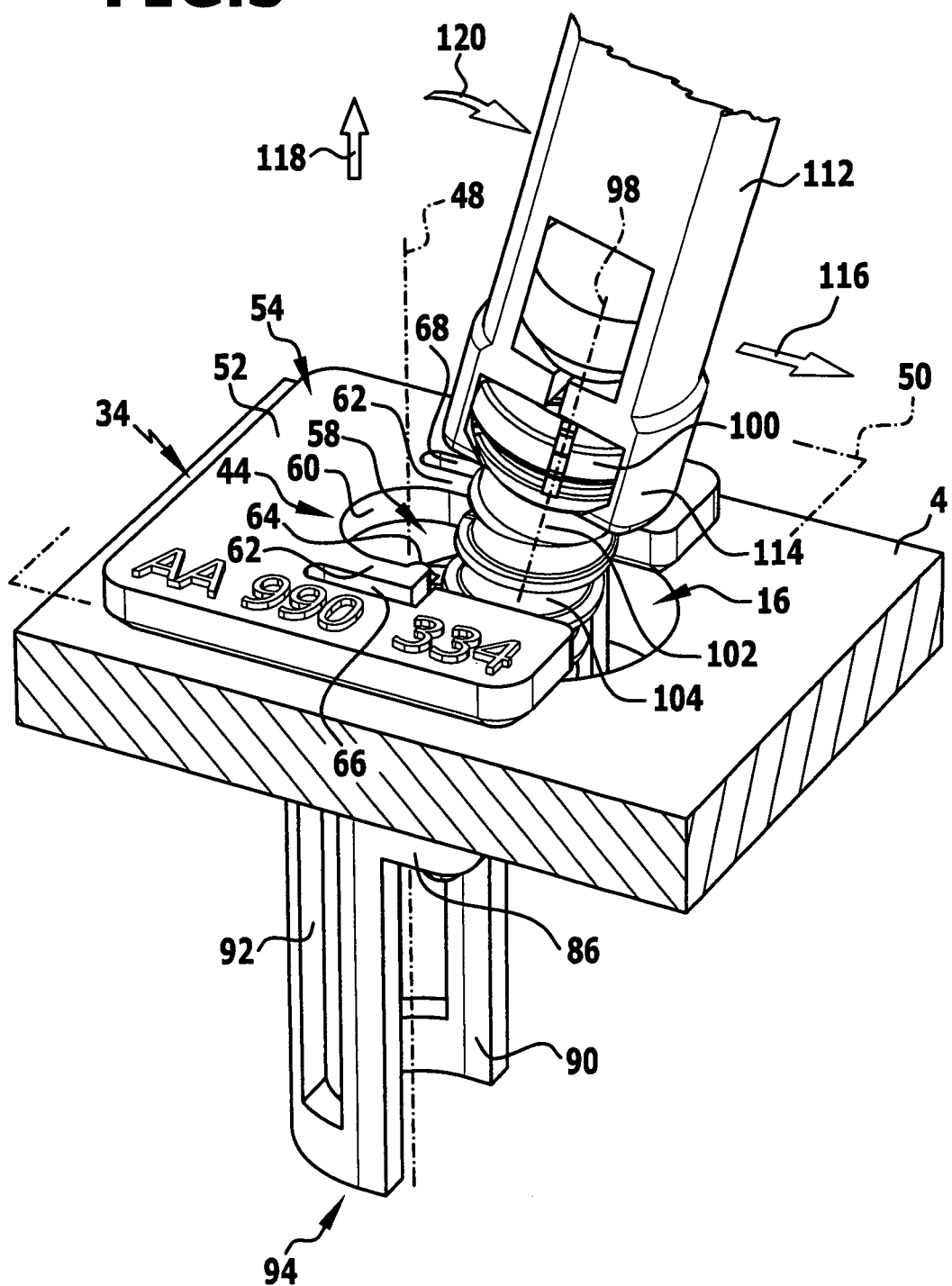
FIG. 5: a view corresponding to FIG. 4, wherein the implant is released from the holding device with the aid of a removing tool.

In order to bring the implant 42 from its first holding position illustrated in FIG. 4 into the first release position illustrated in FIG. 5, a removing tool 112 can be used. The removing tool 112 has a tool head 114 which is designed to engage around the implant section 104. The removing tool 112 can be formed by a screwdriver which can also be used for screwing the external thread 106 of the implant 42 into a body part to be treated.

In order to bring the first connecting device 44 from its first connecting position illustrated in FIG. 4 into the first release position, the removing tool 112 can be moved such that the implant 42 is handled in a first handling direction, which is designated in FIG. 5 as 116, in a direction at right angles to the holding axis 48 so that the implant section 102 is moved out of the implant receptacle 58 within the holding plane 50. In this respect, a first releasing force must be applied and this is determined by the resistance of the holding elements 62 which move within the holding plane 50 in opening directions 70 (cf. FIG. 3) into the adjoining spaces 66 and 68 for the release of the implant section 102.

As soon as the implant 42 has been moved out of the implant receptacle 58 to such an extent that it takes up the first release position, the implant 42 can be removed from the holding device 34 in a direction parallel to the holding axis 48. In this respect, the holding device 34 remains on the plate 4 of the storage unit 2. This is due to the fact that the second connecting device 46 can be actuated independently of the first connecting device 44. The first connecting device 44 is transferred from the first connecting position into the first release position by the first releasing force being applied. In this respect, the second connecting device 46 remains in the second connecting position illustrated in FIGS. 4 and 5 and so the holding device 34 remains connected to the storage unit 2.

In order to transfer the second connecting device 46 into the second release position so that the holding device 34 can be released from the storage unit 2, the holding device 34 can be handled in a handling direction 118 in a direction parallel to the holding axis 48 and moved out of the receptacle 16 of the plate 4. For this purpose, a pressure force can be applied, for example, from the free end 94 of the securing section 90 in the direction of the second handling direction 118. As a result of this, a second releasing force can be applied which deforms the connecting element 78 in the direction of the holding axis 48 whilst abutting on the section 24 of the plate 4 so that the second connecting device 46 is transferred from the second connecting position into the second release position. As a result of this, the holding device 34 can be released from the plate 4.

The first handling direction 116 and the second handling direction 118 extend at right angles to one another. It is understood that the transfer of the first connecting device 44 from the first connecting position into the first release position can be aided by tilting of the implant 42 through an angle of tilt 120 relative to the holding axis 48. In this case, the first handling direction 116 and the second handling direction 118 can be oriented at an angle to one another which corresponds to a right angle plus the angle of tilt 120.

Figure 6:
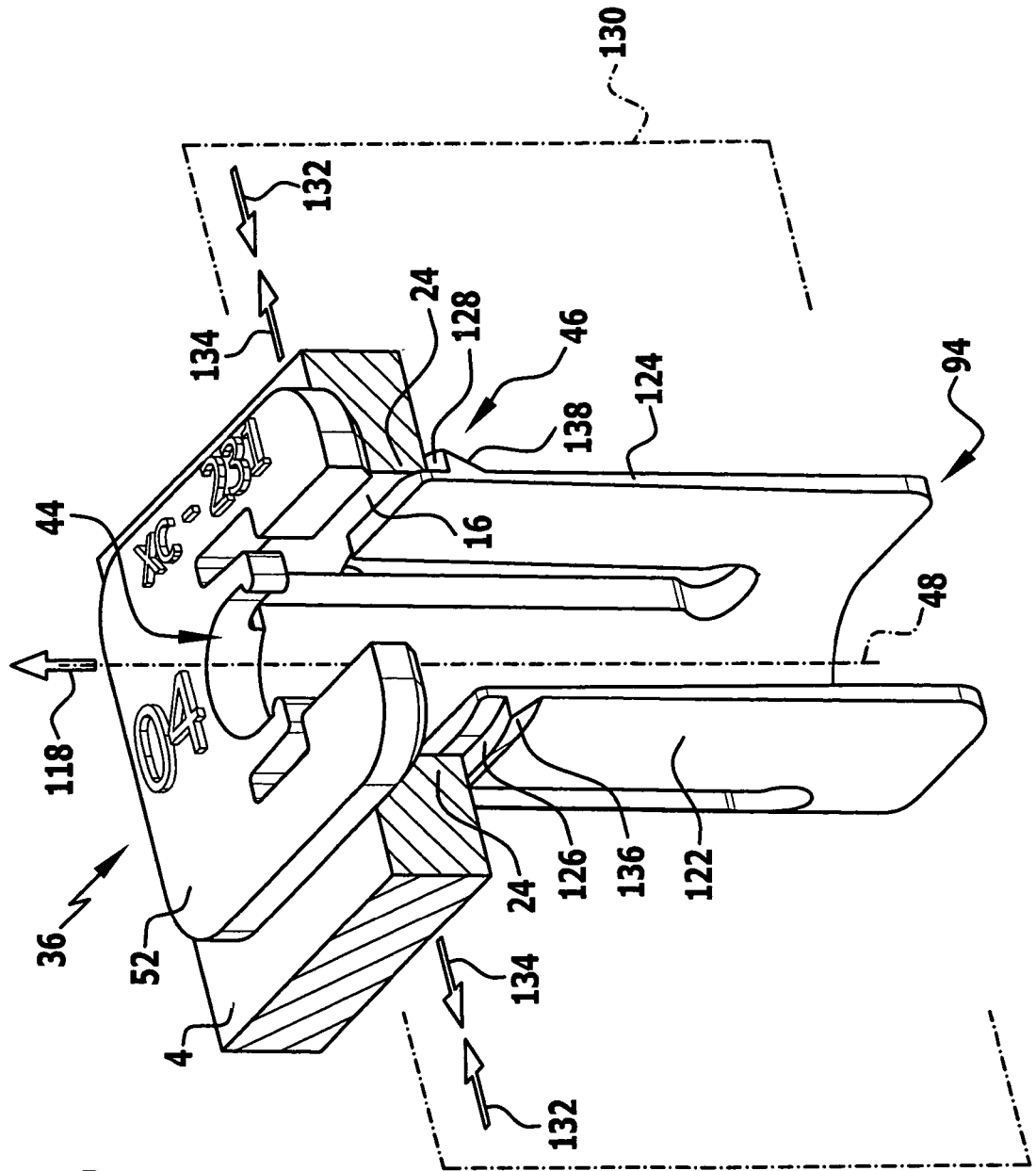
FIG. 6: a perspective view of a holding device according to a second embodiment and a section of the storage unit according to FIG. 1.
Figure 7:
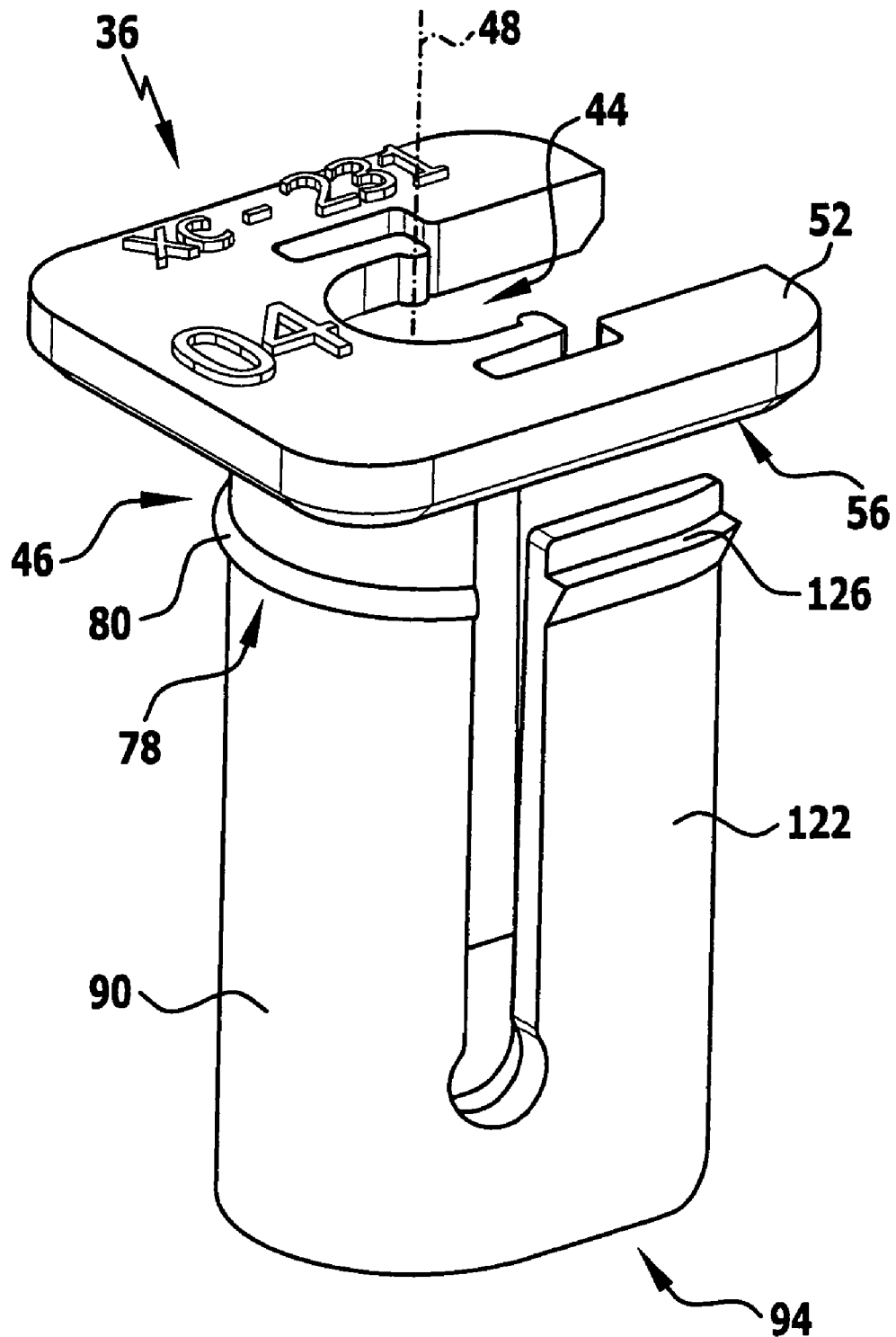
FIG. 7: a view of the holding device according to FIG. 6 from a perspective turned through approximately 90° in relation to FIG. 6.

The holding device 36 illustrated in FIGS. 6 and 7 has a construction similar to that of the holding device 34. In the following, only the differences between the holding devices 34 and 36 will be explained in detail. In contrast to the holding device 34, the holding device 36 has not only a connecting element 78 in the form of a curved snap-in element 80 but also two connecting elements 122 and 124 which are arranged opposite one another. They extend parallel to the holding axis 48 and are connected to the securing section 90 at the free end 94 of the holding device 36.

The connecting elements 122 and 124 each have a snap-in element 126 and 128, respectively, at their ends facing the basic member 52 of the holding device 36. These snap-in elements are arranged at the same level as the snap-in element 80 when seen along the holding axis 48. The connecting elements 122 and 124 are movable and deformable on their own and also relative to one another within a connecting plane 130 such that the snap-in elements 126 and 128 can be moved towards one another within the connecting plane 130 in opening directions 132 opposite to one another. As a result of this, the second connecting device 46 of the holding device 36 can be transferred from its second connecting position illustrated in FIG. 6 into the second release position. When the connecting elements 122 and 124 are spaced so near to one another in the area of the snap-in elements 126 and 128 that the snap-in elements 126 and 128 can be disengaged from the section 24 of the plate 4, the holding device 36 can be brought from the second holding position into the second release position (cf. FIG. 7) in a second handling direction 118 parallel to the holding axis 48.

Once the connecting elements 122 and 124 and the snap-in elements 126 and 128 have been disengaged from the receptacle 16 of the plate 4, the connecting elements 122 and 124 move back again in closing directions 134 opposite to one another of their own accord within the connecting plane 130 such that in the second release position of the holding device 36 the second connecting device 46 is again transferred into the second connecting position. In order to be able to connect the holding device 36 to the storage unit 2 again, the free end 94 of the securing section 90 can be introduced into the receptacle 16 until beveled run-on surfaces 136 and 138 formed by the snap-in elements 126 and 128 engage with the sections 24 of the plate 4. As a result of this, the connecting elements 122 and 124 are moved towards one another in opening directions 132 so that the second connecting device 46 is transferred into the second release position. The beveled run-on surfaces 136 and 138 are introduced into the receptacle 16 to such an extent that the snap-in elements 126 and 128 engage interlockingly behind the section 24 of the plate 4 and, therefore, the second connecting device 46 again takes up the second connecting position.

Figure 8:
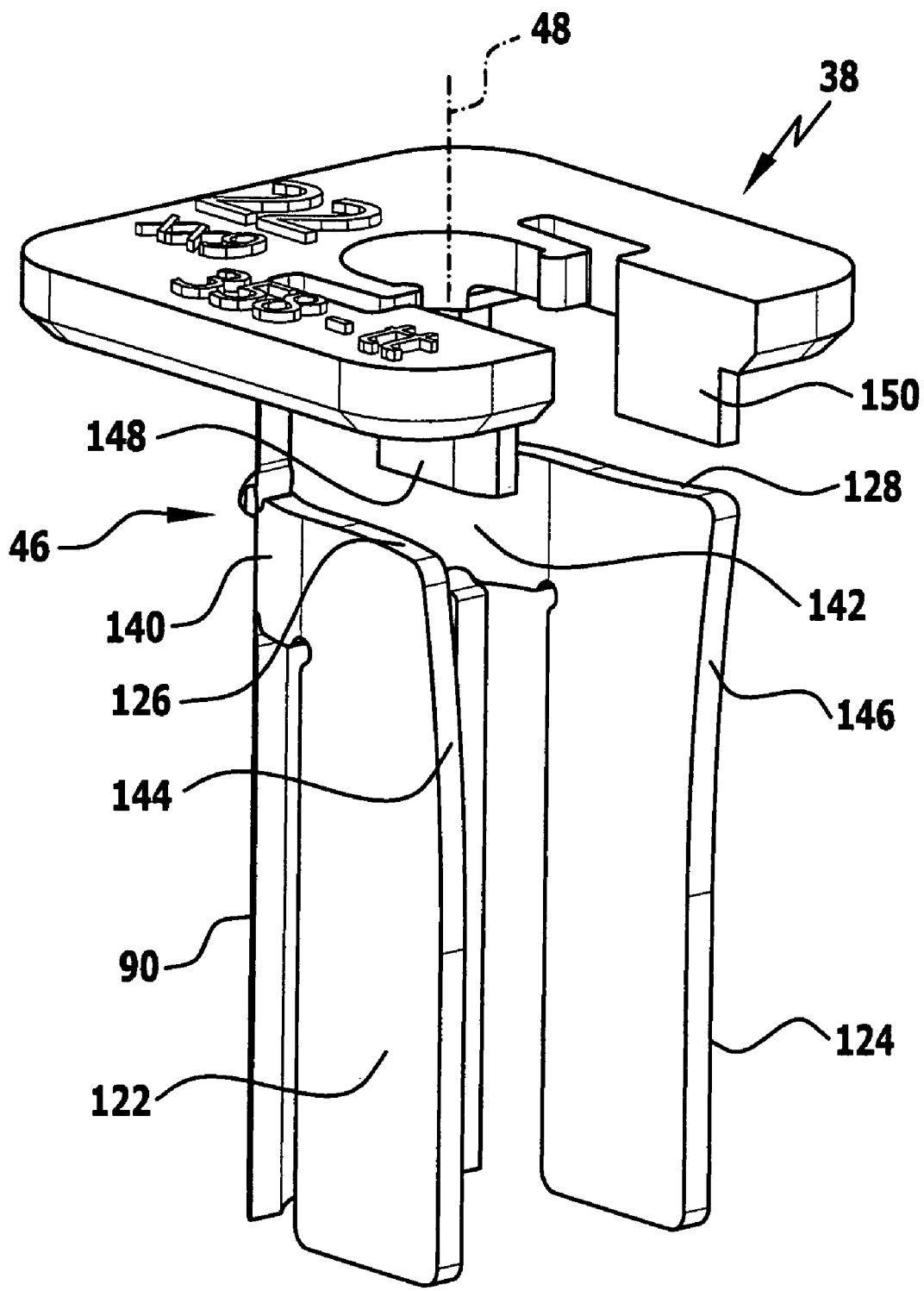
FIG. 8: a perspective view of a holding device according to a third embodiment.
Figure 9:
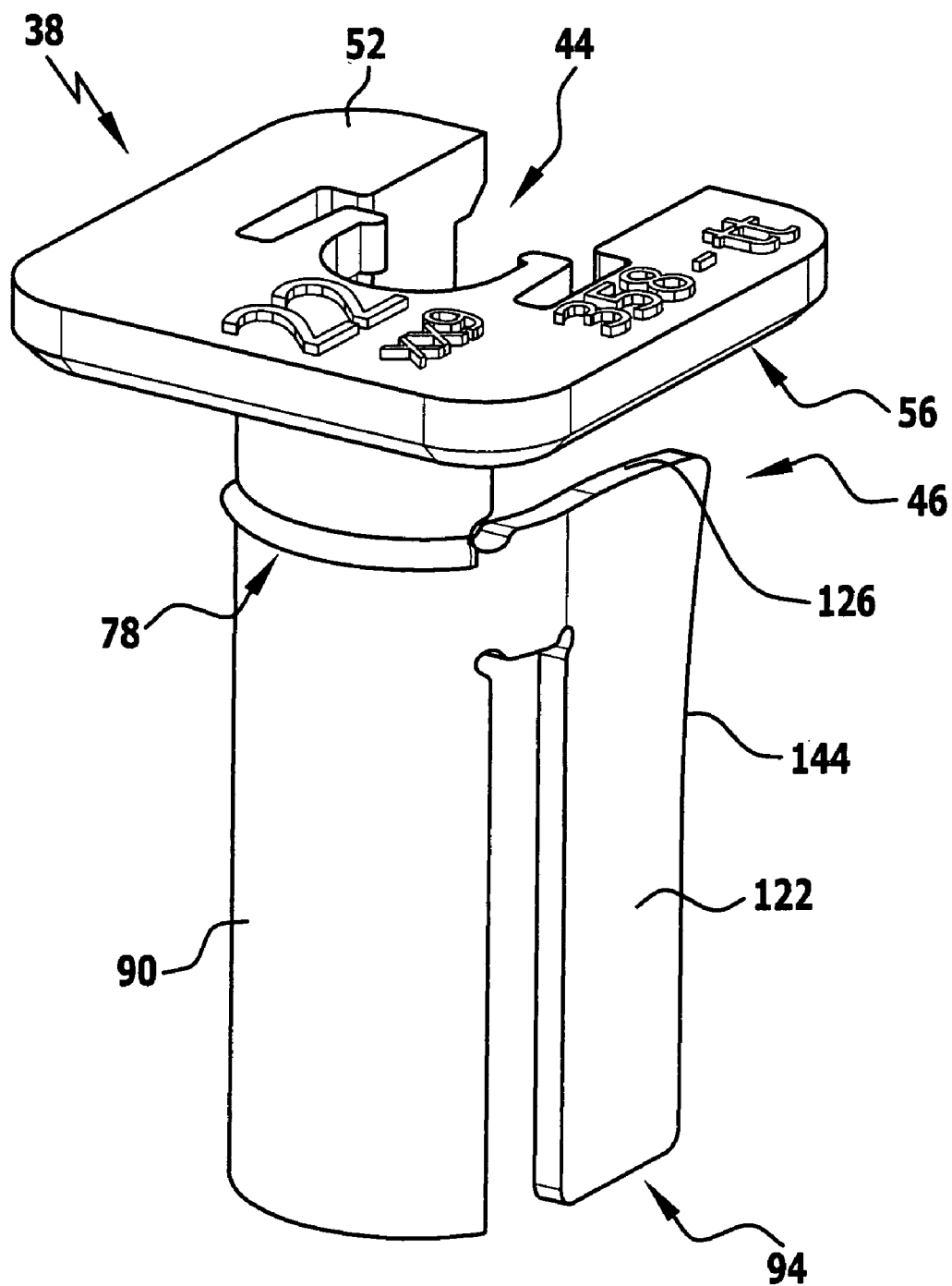
FIG. 9: a view of the holding device according to FIG. 8 from a perspective turned through approximately 90° in relation to FIG. 8.

The holding device 38 illustrated in FIGS. 8 and 9 has a construction similar to that of the holding device 36. In the following, only the differences between the holding devices 36 and 38 will, therefore, be explained in detail. The connecting elements 122 and 124 of the holding device 38 which extend parallel to the holding axis 48 are not connected to the securing section 90 at the free end 94 thereof but rather via attachments 140 and 142 which are provided adjacent to the connecting element 78. The snap-in elements 126 and 128 are not designed in the form of projections, as in the holding device 36 according to FIGS. 6 and 7, but are formed by edge surfaces of the connecting elements 122 and 124 pointing in the direction towards the contact surface 56 of the basic member 52. The connecting elements 122 and 124 have, in addition, two edge sections 144 and 146 which are slightly inclined in their course relative to the holding axis 48 and make the introduction of the free end 94 into a receptacle 16 of the plate 4 easier.

In order to be able to position the holding device 38 exactly relative to a receptacle 16 of the plate 4 of the storage unit 2, the holding device 38 has guiding sections 148 and 150 which extend parallel to the holding axis 48 proceeding from the contact surface 56 and each abut on a section 24 of the plate 4 in the second holding position of the holding device 38.

Figure 10:
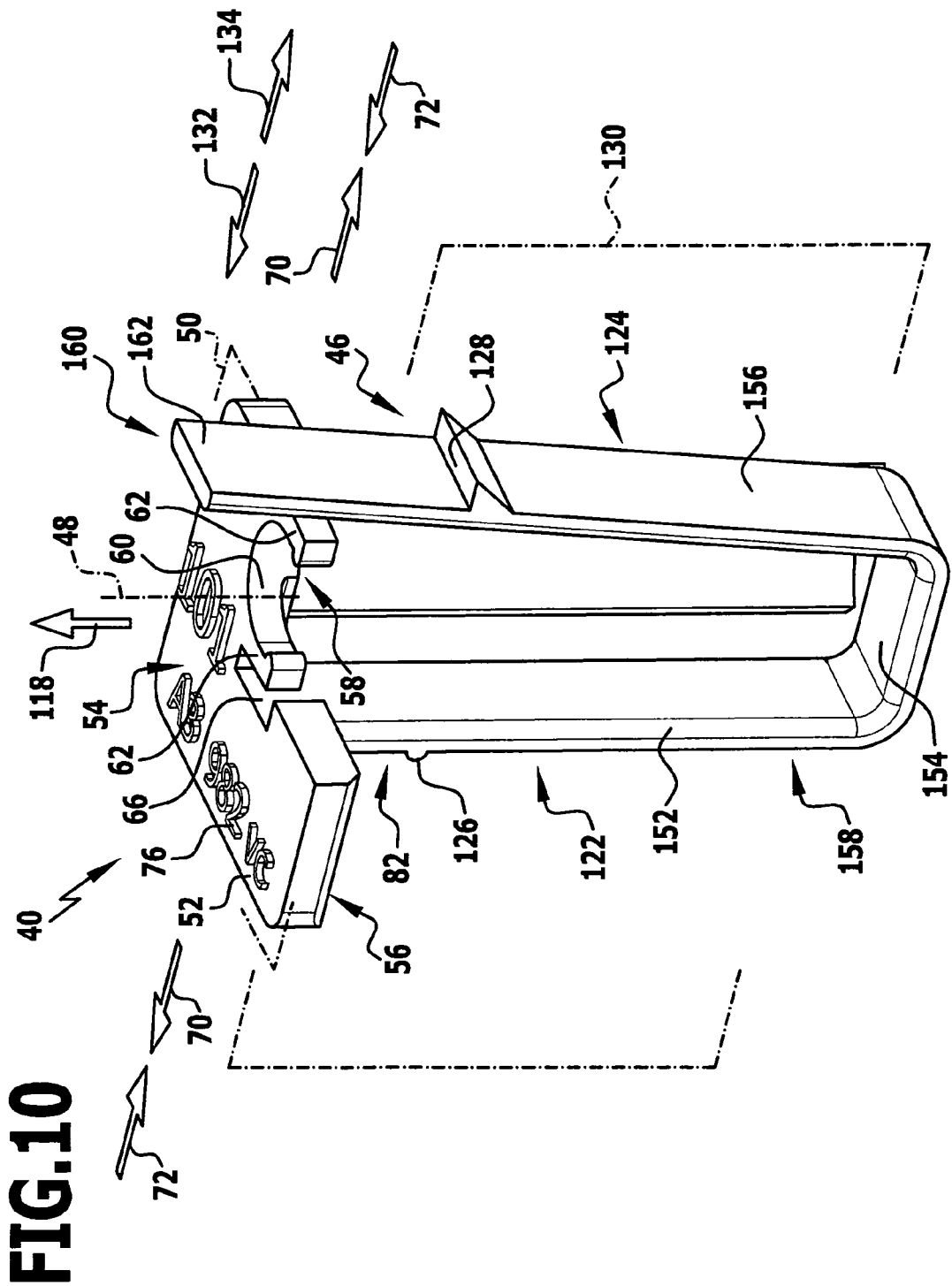
FIG. 10: a perspective view of a holding device according to a fourth embodiment.
Figure 11:
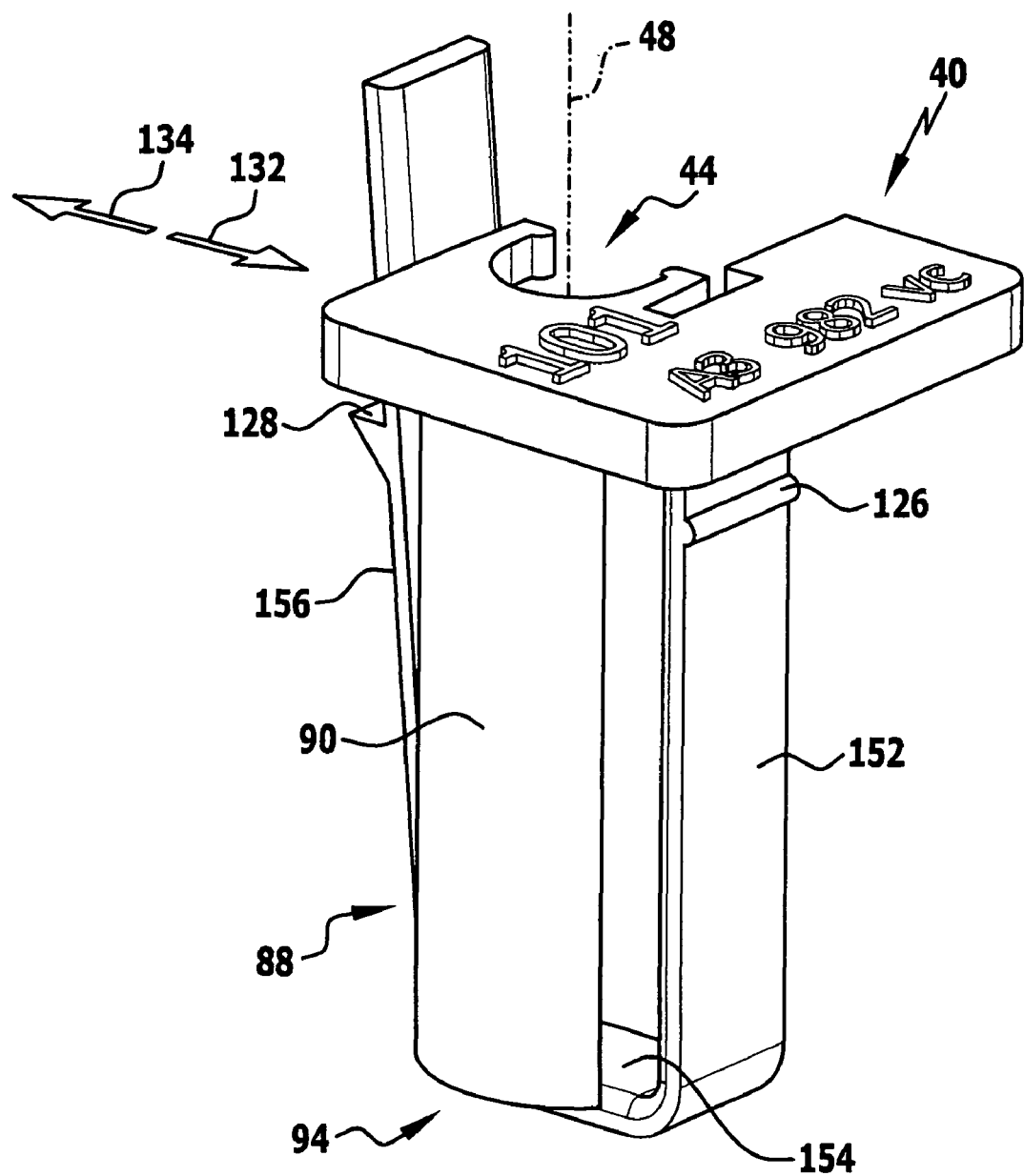
FIG. 11: a view of the holding device according to FIG. 10 from a perspective turned through approximately 180° in relation to FIG. 10.

The holding device 40 illustrated in FIGS. 10 and 11 differs, inter alia, from the holding devices 34, 36 and 38 described thus far in that it defines a holding axis 48 which does not essentially extend centrally through the basic member 52 but is offset to the side in relation thereto. This has the advantage that a particularly large visible surface 54 results, on which a relatively large number of implant data 76 can be displayed closely adjacent to one another but easy to read.

The implant receptacle 58 of the holding device 40, which is limited by two holding elements 62 located opposite one another as well as the contact section 60 of the basic member 52, is offset to such an extent out of the center of the basic member 52 that the space 68 present in the case of the holding devices 34, 36 and 38 is no longer applicable or is formed by the surroundings of the holding device 40.

The second connecting device 46 of the holding device 40 comprises, in a similar way to the holding devices 36 and 38, two connecting elements 122 and 124 extending essentially parallel to the holding axis 48. In contrast to the holding devices 36 and 38, the connecting elements 122 and 124 of the holding device 40 are provided separate from the securing section 90 of the securing device. A first connecting element 122 is designed, for example, as a leg 152 of a U which extends parallel to the holding axis 48 proceeding from the contact surface 56 of the basic member 52 as far as the free end 94 of the securing section 90. Here, the leg 152 of the U merges into a base 154 of the U which extends parallel to the basic member 52 and, therefore, to the holding plane 50. At its end located opposite the leg 152 of the U the base 154 of the U ends at a leg 156 of the U which forms the connecting element 124. The legs 152 and 156 of the U and the base of the U together form a U-shaped material section 158. The leg 156 of the U extends from the base 154 of the U approximately parallel to the holding axis 48 in the direction towards the basic member 52 and—in the area of a free end 160 which is not connected to the basic member 52—as far as an actuating element 162. The actuating element 162 is designed in the form of a gripping section. This gripping section and the connecting elements 122 and 124 are arranged on oppositely located sides of the basic member 52 when seen along the holding axis 48.

In order to connect the holding device 40 illustrated in FIGS. 10 and 11 to the storage unit 2 illustrated in FIG. 1, the free end 94 of the holding device 40 can be inserted into one of the receptacles 16 of the plate 4. The second connecting device 46 of the holding device 40 is hereby transferred from the second connecting position into the second release position with deformation of the connecting element 124 in the direction towards the holding axis 48 which corresponds to an opening direction 132. When the holding device 40 is inserted into one of the receptacles 16 to such an extent that the snap-in elements 126 and 128 can engage interlockingly behind associated sections 24 of the receptacle 16, the connecting element 124 springs back into the position illustrated in FIG. 10 in accordance with a closing direction 134 so that the second connecting device 46 is transferred into the second connecting position.

In order to transfer the second connecting device 46 from the second connecting position into the second release position, the actuating element 162 can be actuated in accordance with the opening direction 132 which extends at right angles to the holding axis 48. In this respect, the connecting element 124 or rather the leg 156 of the U is deformed within a connecting plane 130 so that the snap-in element 128 can disengage from the associated section 24 of the plate 4, whereby the second connecting device 46 is transferred into the second release position. In this way, the holding device 40 can be released from the storage unit 2 during its movement in accordance with a second handling direction 118 which extends parallel to the holding axis 48.

The legs 152 and 156 of the U of the holding device 40 are arranged on oppositely located sides relative to the holding axis 48. This has the advantage that an implant 42 connected to the holding device 40 via the first connecting device 44 is protected from mechanical influences not only by the securing section 90 but also with the aid of the U-shaped material section 158. In this respect, the base 154 of the U shields the implant 42 in relation to the mounting surface 14 illustrated in FIG. 1 when the holding device 40 is connected to the storage unit 2.

Figure 12:
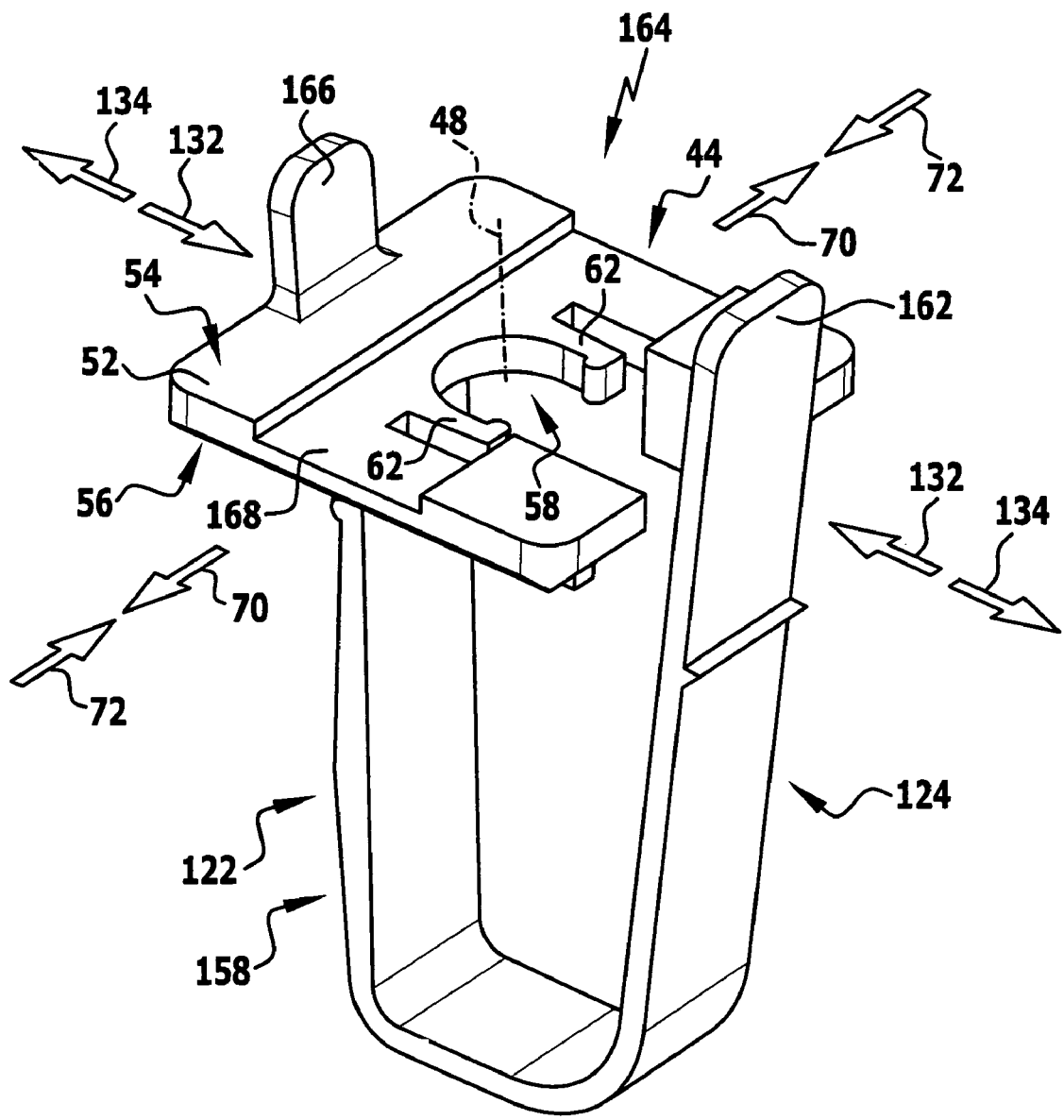
FIG. 12: a perspective view of a holding device according to a fifth embodiment.
Figure 13:
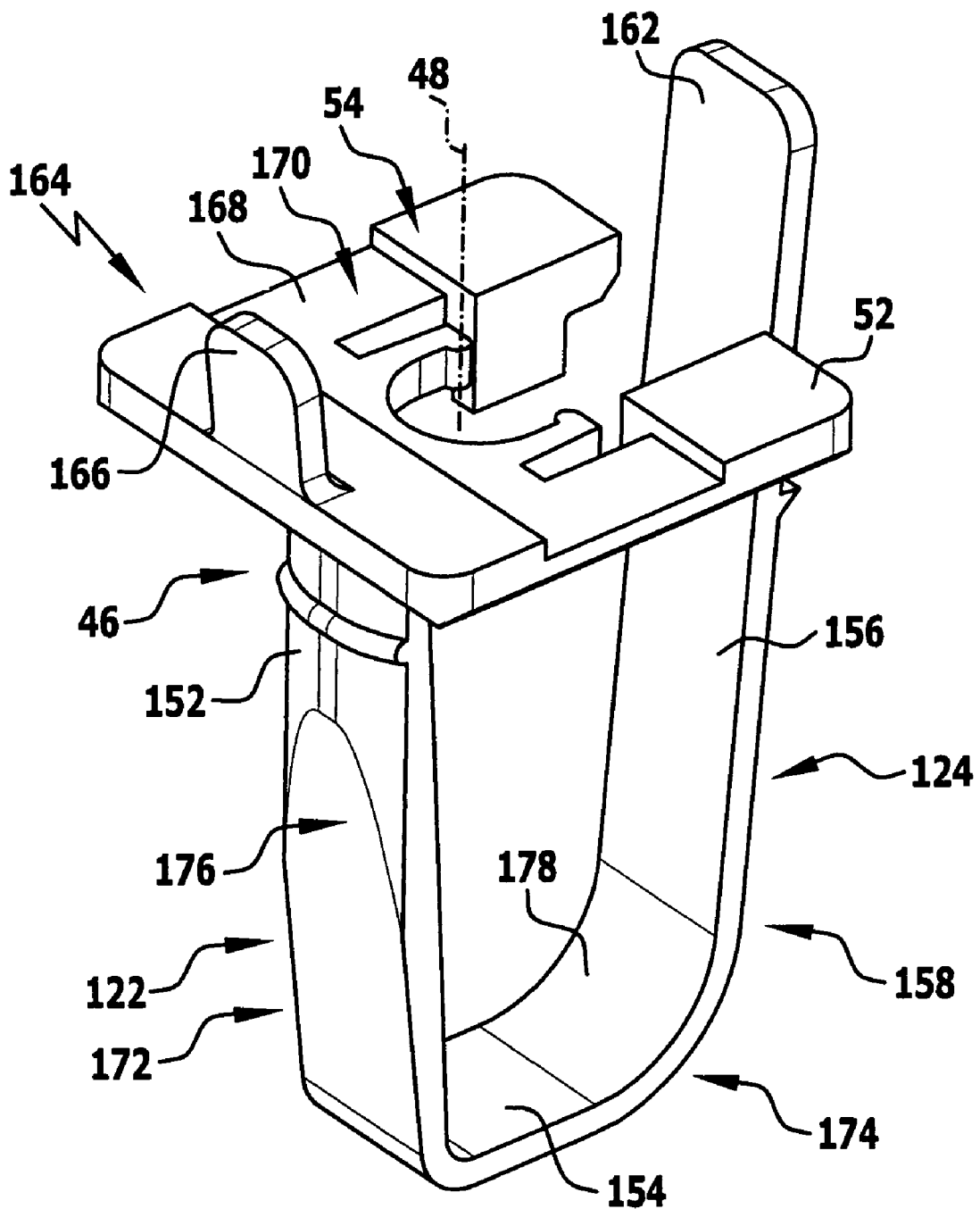
FIG. 13: a view of the holding device according to FIG. 12 from a perspective turned though approximately 120° in relation to FIG. 12.

FIGS. 12 and 13 illustrate an additional holding device 164. This likewise comprises a U-shaped material section 158. In contrast to the holding device 40 according to FIGS. 10 and 11, the holding axis 48 of the holding device 164 extends approximately centrally through the basic member 52. In addition, the holding elements 62 of the first connecting device 44 are oriented in such a manner that their opening and closing directions 70 and 72 do not extend parallel to the opening directions 132 and closing directions 134 of the connecting elements 122 and 124, as in the case of the holding device 40, but rather at right angles to one another.

The holding device 164 has, in addition, an actuating element 166 which is rigidly connected to the basic member 52, projects beyond the visible surface 54 and extends approximately parallel to the holding axis 48. The actuating elements 162 and 166 are arranged on oppositely located sides of the holding axis 48 and can be moved relative to one another in the specified opening directions 132 and closing directions 134, respectively, in order to transfer the second connecting device 46 from the second connecting position into the second release position.

The basic member 52 has a reduced material thickness in a central section 168. The central section 168 has a surface 170 which extends parallel to the visible surface 54 of the basic member 52 and is spaced at a smaller distance from the contact surface 56 of the basic member 52 than the visible surface 54. As a result of this, the surface 170 is set back in comparison with the visible surface 54. When the holding device 164 is connected to an implant 42 with the aid of its first connecting device 44, an implant section 100 (cf. FIG. 3) does not extend beyond the visible surface 54 or only slightly. As a result of this, the holding device 164 and an implant 42 can be supplied together to an inscription device, with which implant data 76 can be applied to the visible surface 54 of the holding device 164, for example, by way of overprinting.

The holding device 164 illustrated in FIGS. 12 and 13 differs, in addition, from the holding device 40 illustrated in FIGS. 10 and 11 in that its U-shaped material section 158 has insertion aids 172 and 174. The insertion aid 172 comprises an insertion surface 176 extending at a slight angle to the holding axis 48. The insertion aid 174 is formed by a partially cylindrical transition section between the base 154 of the U and the leg 156 of the U. The insertion aids 172 and 174 make the insertion of the holding device 164 into a receptacle 16 of the storage unit 2 easier.

Figure 14:
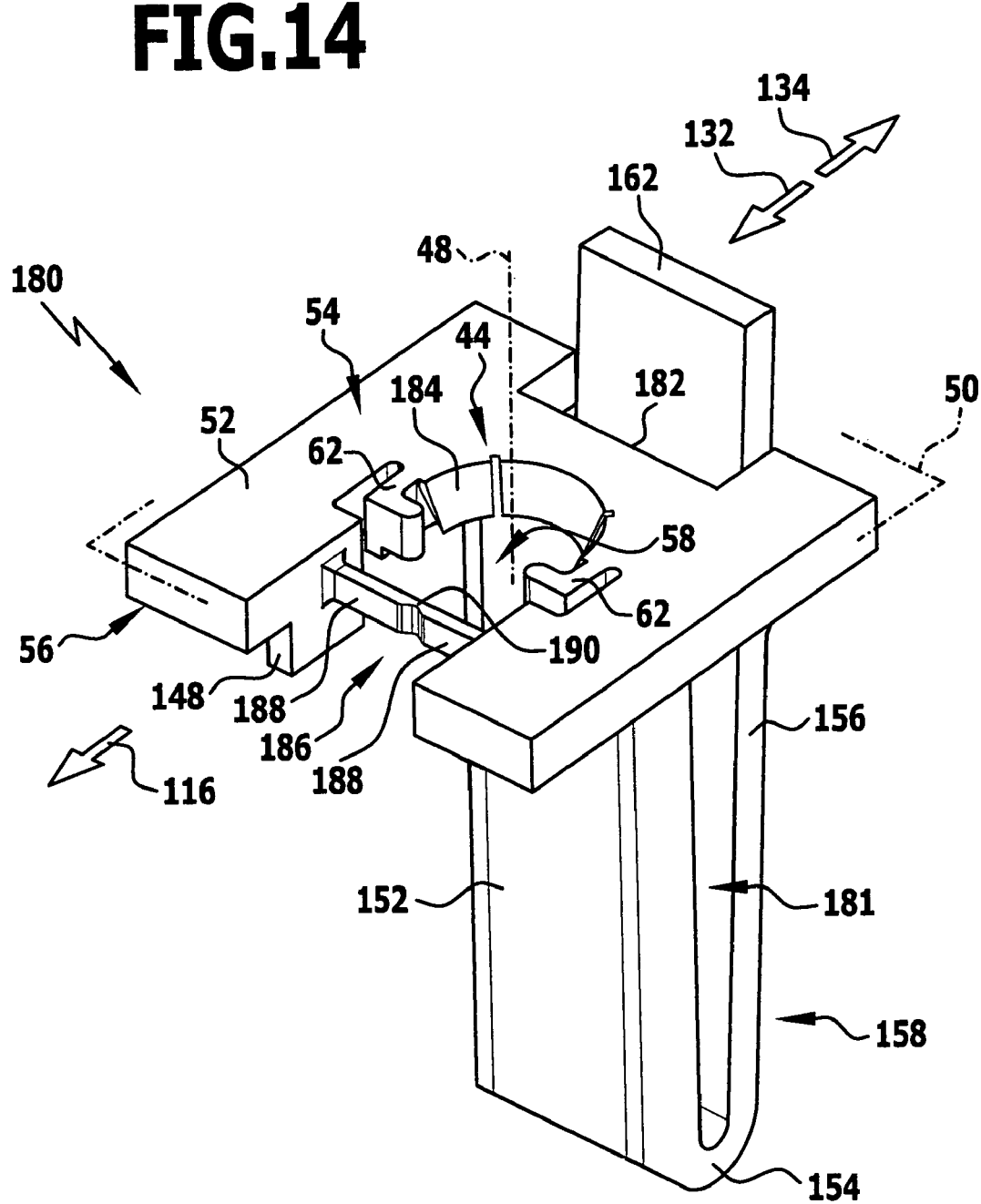
FIG. 14: a perspective view of a holding device according to a sixth embodiment.
Figure 15:
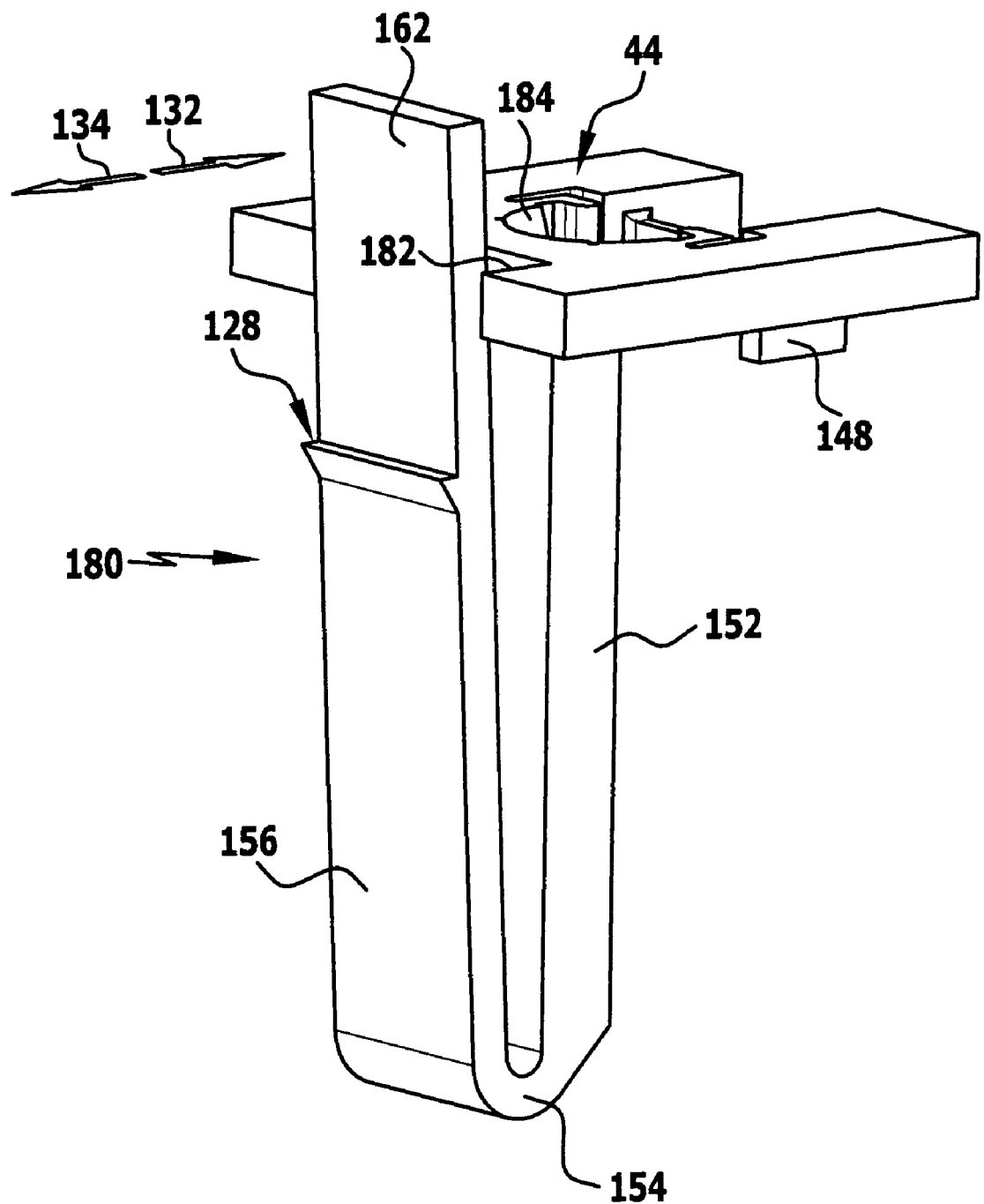
FIG. 15: a view of the holding device according to FIG. 14 from a perspective turned through approximately 150° in relation to FIG. 14.

FIGS. 14 and 15 illustrate a further holding device 180. This differs from the holding devices 40 and 164 due to the fact that its U-shaped material section 158 is designed in such a manner that the legs 152 and 156 of the U are immediately adjacent to one another. The holding axis 48 of the holding device 180 extends outside a space 181 formed between the legs 152 and 156 of the U.

The basic member 52 of the holding device 180 has a recess 182 extending within the holding plane 50. This creates a space for movement of the leg 156 of the U which can be moved in opening direction 132 or in closing direction 134 with the aid of the actuating element 162.

The implant receptacle 58 of the first connecting device 44 of the holding device 180 differs from the implant receptacles of the holding devices 34, 36, 38, 40, 164 described thus far in that the holding elements 62 which are located opposite one another are comparatively short. Instead of a rigid contact section 60 (cf. FIG. 2), the implant receptacle 58 of the holding device 180 has contact elements 184 in the shape of circular segments. They are of a lug-shaped design and connected to the basic member 52 at the level of the visible surface 54 thereof. The contact elements 184 extend at an angle in the direction towards the holding axis 48 proceeding from the visible surface 54.

When an implant 42 is connected to the holding device 180 with the aid of the first connecting device 44, the contact elements 184 abut on the implant section 102 (cf. FIG. 3) under tension. As a result of this, the implant 42 is connected to the holding device 180 without any clearance.

The holding device 180 comprises an indicating device 186, with which it can be shown whether the first connecting device 44 of the holding device 180 has been transferred from the first connecting position into the first release position at least once. The indicating device 186 comprises two tape-like indicating elements 188 which extend adjacent to the implant receptacle 58 within the holding plane 50. The indicating elements 188 are connected to one another via a connecting section 190 which forms a predetermined breaking point.

When an implant 42 connected to the holding device 180 is transferred from a first holding position into a first release position in a direction at right angles to the holding axis 48 in accordance with a first handling direction 116, this causes destruction of the connection between the indicating elements 188. As a result of this, it can be clearly ascertained that an implant 42 has already been removed from the holding device 180. As a result of this, any unintentional re-use of the holding device 180 can also be ruled out.

Figure 16:
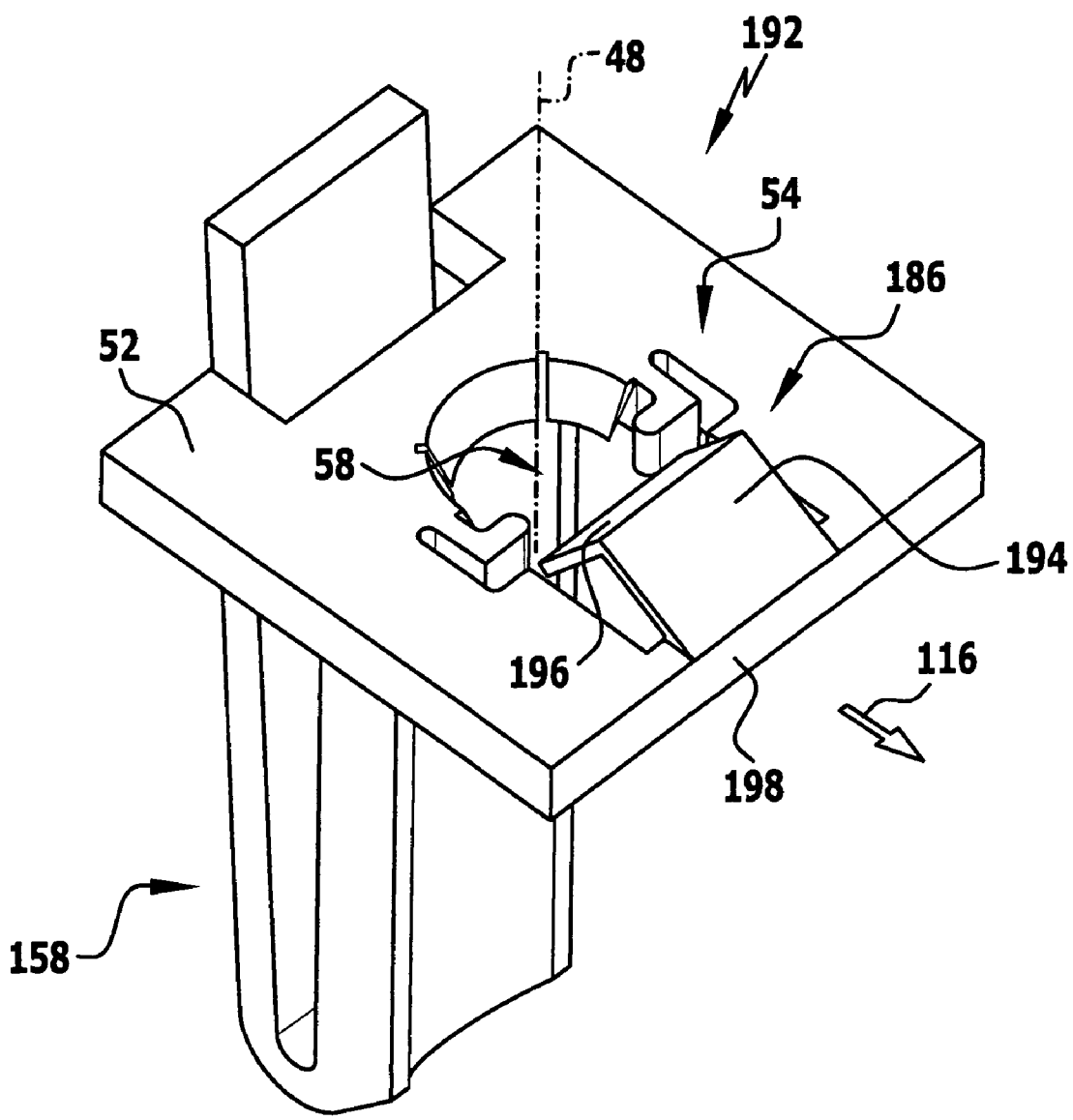
FIG. 16: a perspective view of a holding device according to a seventh embodiment.
Figure 17:
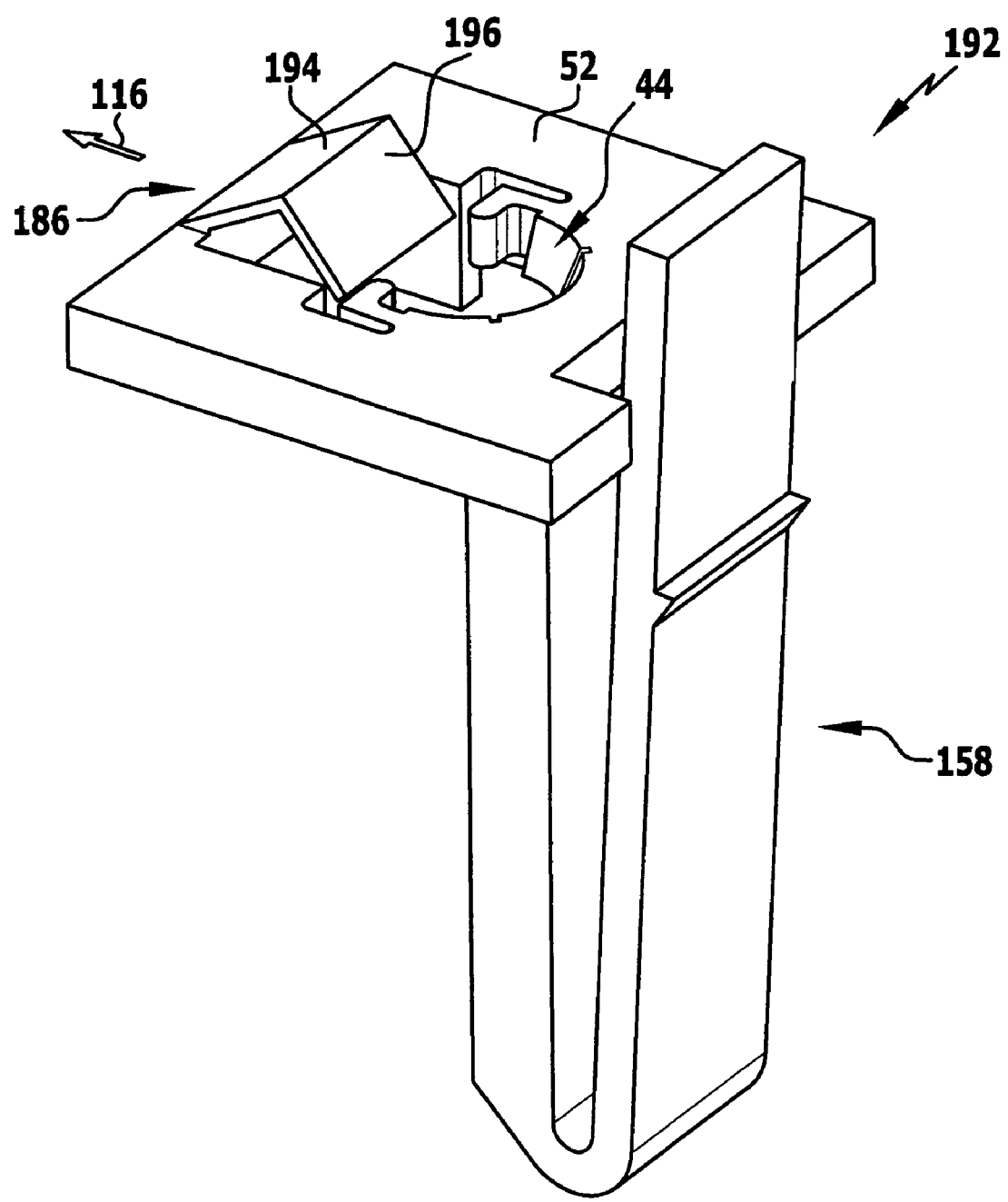
FIG. 17: a view of the holding device according to FIG. 16 from a perspective turned through approximately 150° in relation to FIG. 16.

FIGS. 16 and 17 illustrate an additional holding device 192 which differs from the holding device 180 according to FIGS. 14 and 15 only in its configuration of the indicating device 186. The indicating device 186 of the holding device 192 comprises two element sections 194 and 196 which are arranged at an oblique angle to one another. The element section 194 is articulated to a closed edge 198 of the basic member 52 and extends at an acute angle relative to the visible surface 54 of the basic member 52 in the direction towards the holding axis 48. The element section 196 extends in the direction towards the holding axis 48 as far as adjacent to the implant receptacle 58 proceeding from the end of the element section 194 facing the holding axis 48.

When an implant 42 held on the holding device 192 is transferred from a first holding position into a first release position in a first handling direction 116, the element sections 194 and 196 are deformed permanently and so it can be shown that the first connecting device 44 of the holding device 192 has been transferred from the first connecting position into the first release position.

Figure 18:
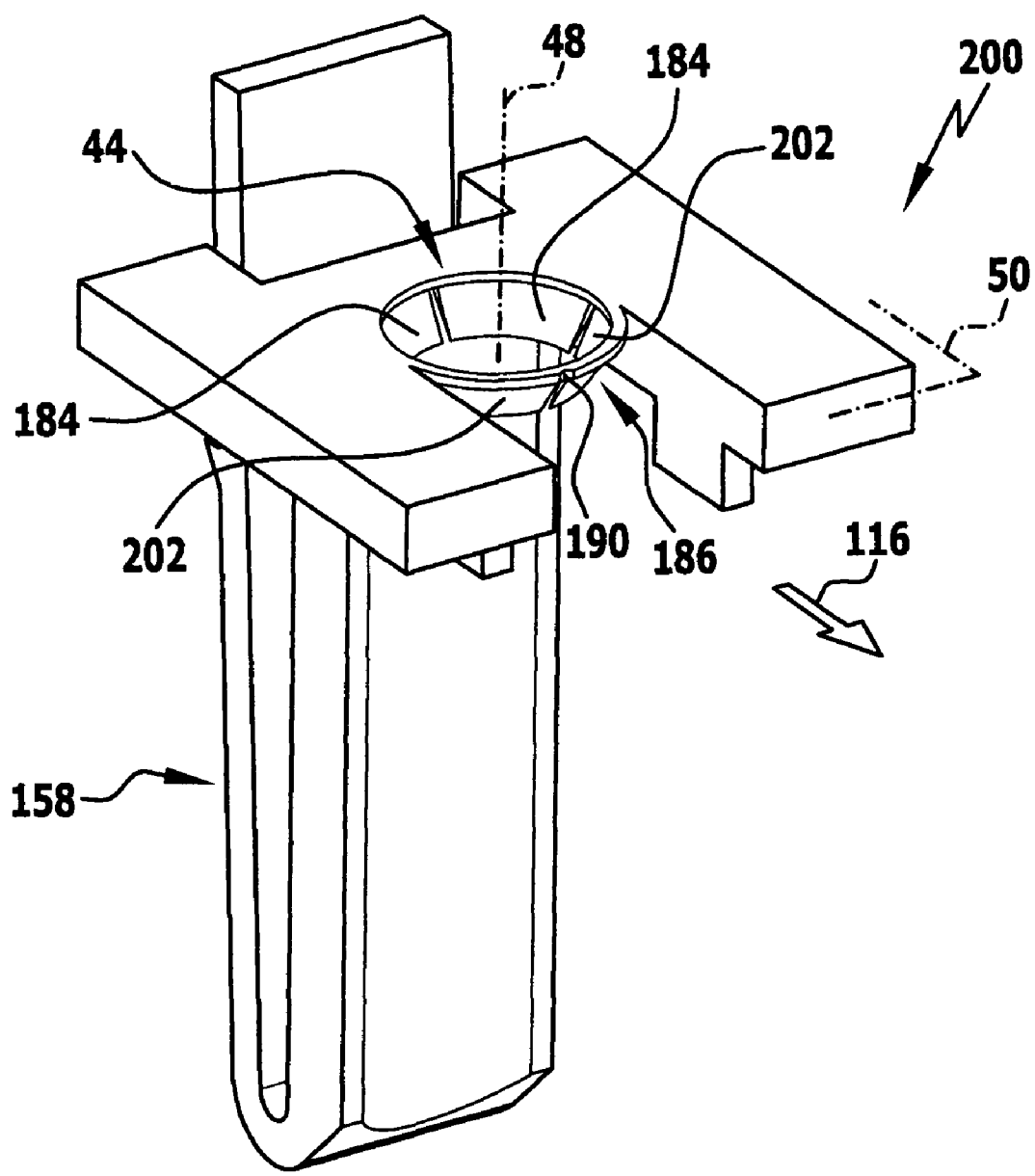
FIG. 18: a perspective view of a holding device according to an eighth embodiment.
Figure 19:
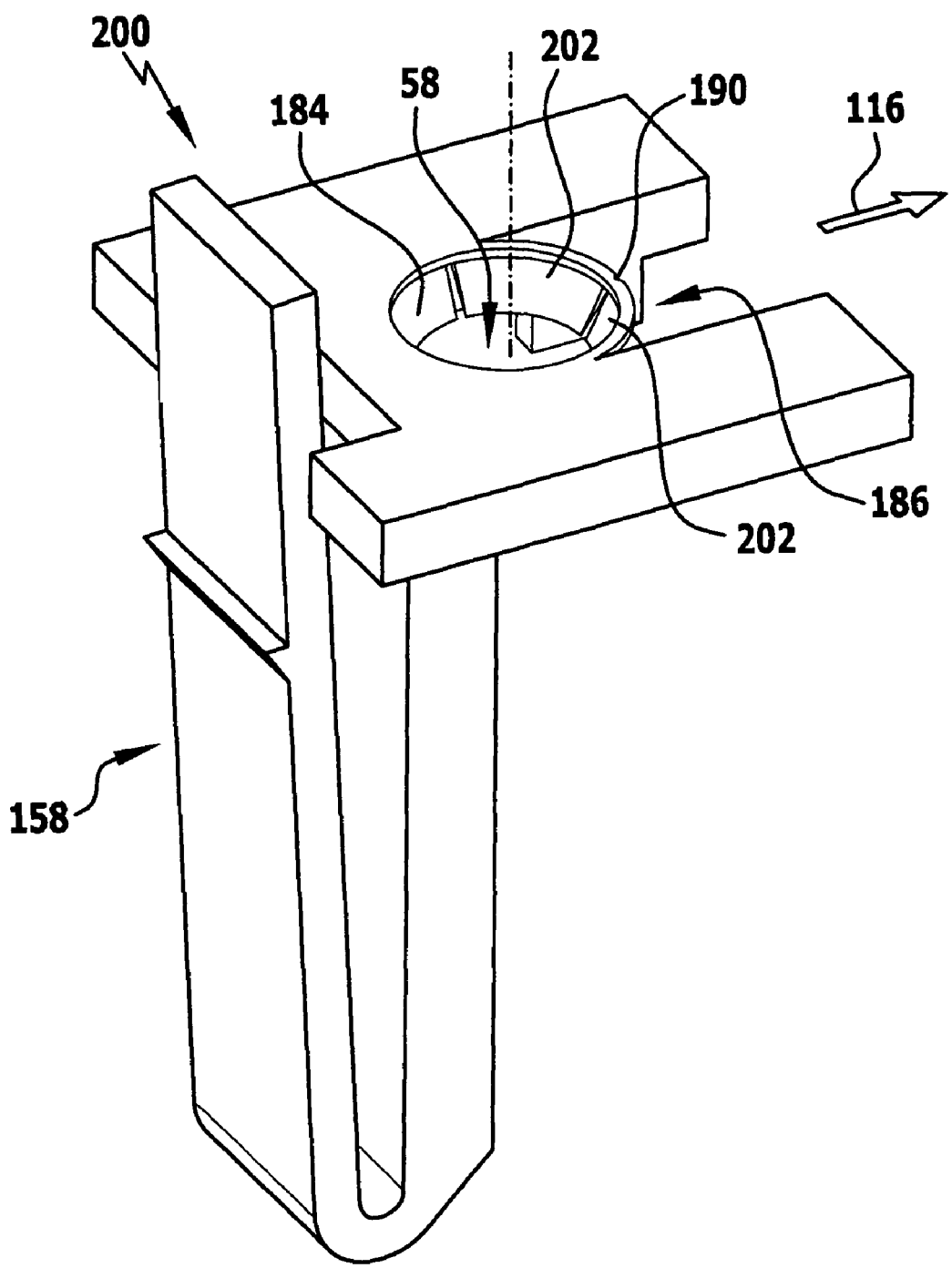
FIG. 19: a view of the holding device according to FIG. 18 from a perspective turned through approximately 90° in relation to FIG. 18.

The holding device 200 illustrated in FIGS. 18 and 19 differs from the holding devices 180 and 192 in its configuration of the first connecting device 44. This likewise comprises contact elements 184 which are in the shape of circular segments but no essentially tongue-shaped holding elements 62 but rather holding elements 202 which are shaped like circular segments and limit an implant receptacle 58, which is completely enclosed on its circumferential side and extends within a holding plane 50, together with the contact elements 184. The holding elements 202 are connected to one another via a connecting section 190 which forms a predetermined breaking point.

An implant 42 can be inserted into the holding device 200 in that it is inserted into the implant receptacle 58 in the direction of the holding axis 48 with its implant section 104 (cf. FIG. 3) first. In this respect, the contact elements 184 and the holding elements 202 are deformed radially outwards by the external thread 106 so that the implant section 104 can be introduced into the implant receptacle completely until the implant section 102 is arranged at the level of the contact elements 184 and the holding elements 202 and the contact elements 184 and the holding elements 202 can be reset again radially inwards. The connecting device 44 then takes up the first connecting position.

In order to release the implant 42 from the holding device 200, the first connecting device 44 can be brought from the first connecting position into the first release position in that the implant 42 is moved out of the implant receptacle 58 in a first handling direction designated as 116. In this respect, the connecting section 190 between the holding elements 202 is destroyed. As a result of this, it can be shown that an implant 42 was already held on the holding device 200 and so any unintentional re-use of the holding device 200 can be ruled out. The holding device 200 therefore likewise comprises an indicating device 186. With this indicating device, the indicating elements are formed by the holding elements 202.

Figure 20:
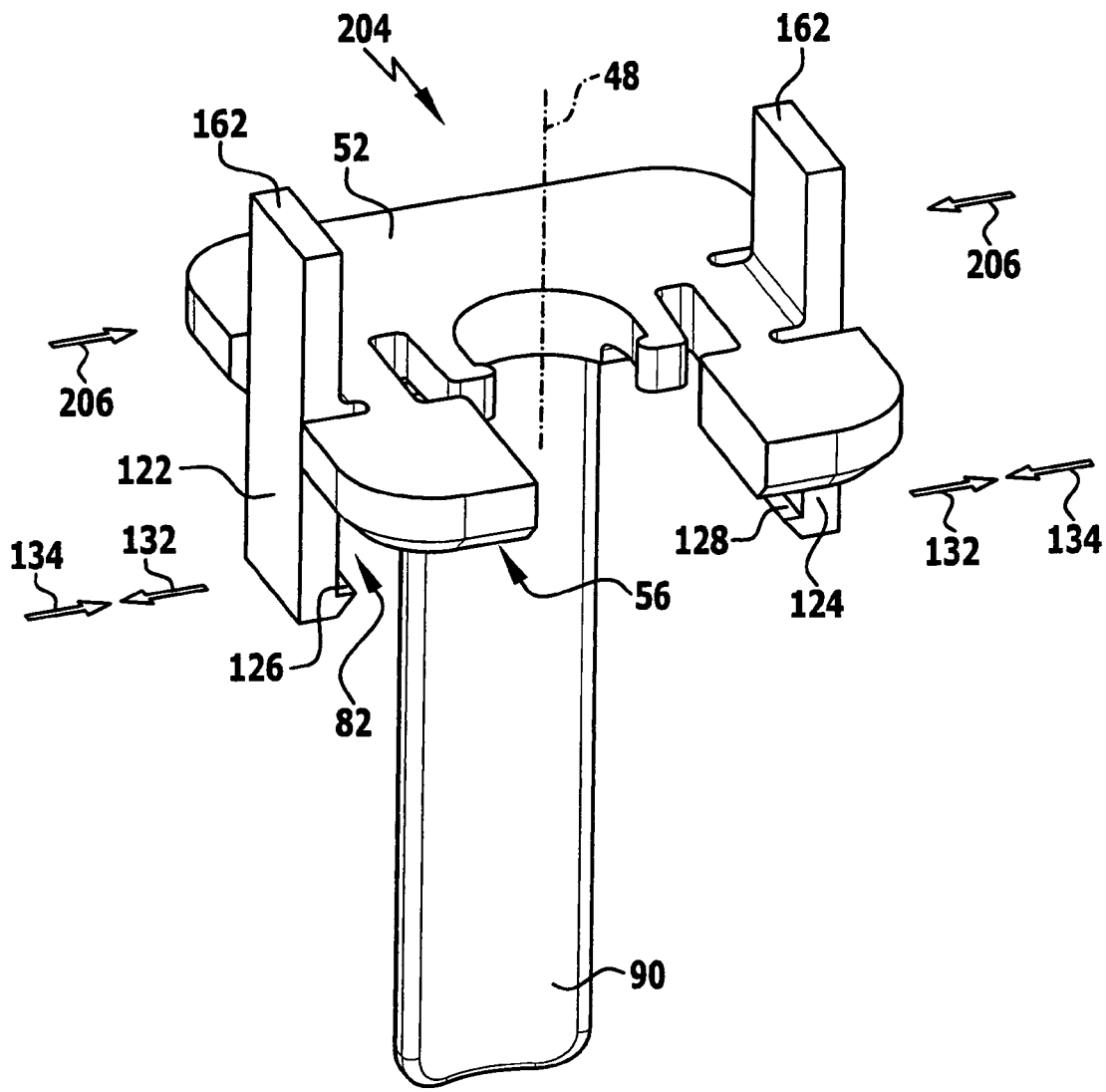
FIG. 20: a perspective view of a holding device according to a ninth embodiment.
Figure 21:
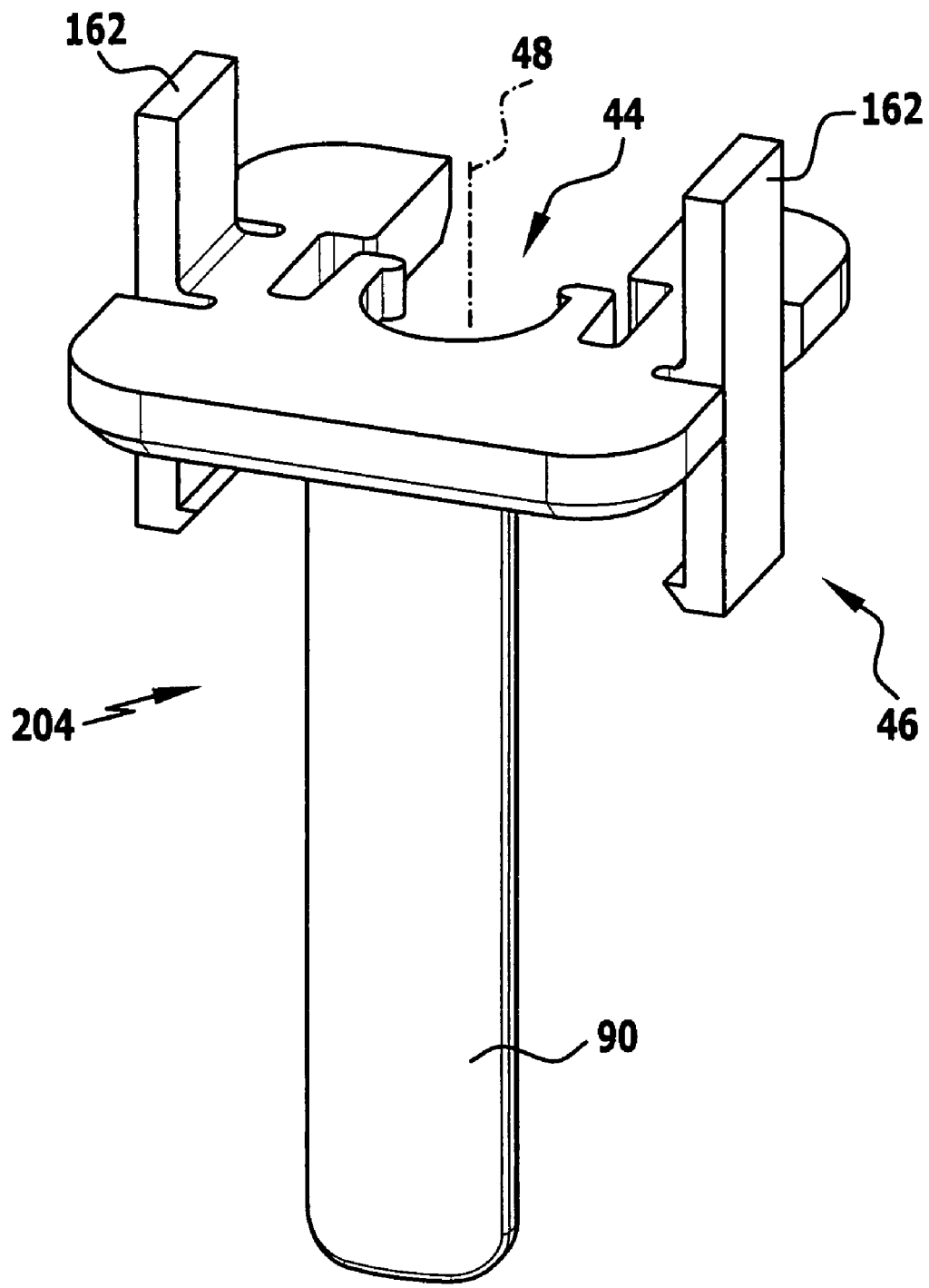
FIG. 21: a view of the holding device according to FIG. 20 from a perspective turned through approximately 150° in relation to FIG. 20.

FIGS. 20 and 21 illustrate a further holding device 204. Its first connecting device 44 has a construction which corresponds, for example, to the construction of the first connecting device 44 of the holding device 34 according to FIG. 2. The holding device 204 likewise has a securing section 90 which corresponds in its construction to the securing section 90 of the holding device 40 according to FIGS. 10 and 11.

On the other hand, the second connecting device 46 of the holding device 204 differs from the second connecting devices 46 of the holding devices 34, 36, 38, 40, 164, 180, 192, 200 due to the fact that the snap-in elements 126 and 128 are arranged on the side of the connecting elements 122 and 124 facing the holding axis 48. This causes a reversal of the corresponding opening directions 132 and the closing directions 134. In addition, an undercut area 82 formed between the snap-in elements 126 and 128 and the contact surface 56 of the basic member 52 is formed between the connecting elements 122 and 124 and not on oppositely located sides.

The holding device 204 can be connected to the storage unit 2 illustrated in FIG. 1 in that the securing section 90 of the holding device 204 dips into a receptacle 16 of the plate 4 until the snap-in elements 126 and 128 engage in the storage areas 32 of the storage elements 26. The second connecting device 46 of the holding device 204 then takes up the second connecting position.

In order to transfer the second connecting device 46 of the holding device 204 into the second release position, the actuating elements 162 of the connecting elements 122 and 124 can be moved towards one another in actuating directions 206 opposite to one another so that the snap-in elements 126 and 128 are moved away from one another in opening direction 132 and disengage from the storage areas 32 of the storage elements 26.

The invention claimed is:

1. Holding device for an implant, comprising:
   a first connecting device for releasably connecting the holding device and the implant,
   the first connecting device being transferable from a first connecting position, an implant being connectable or connected to the holding device in said first connecting position, into a first release position, the holding device releasing the implant in said first release position,
   an indicating device indicating an at least one-time transfer of the first connecting device from the first connecting position into the first release position, and
   a second connecting device for releasably connecting the holding device and a storage unit,
   wherein:
      the first connecting device is designed in such a manner that the implant is adapted to be handled in a first handling direction during movement from a first holding position, the implant being connected to the holding device in said first holding position, into the first release position,
      the second connecting device is designed in such a manner that the holding device is adapted to be handled in a second handling direction during movement from a second holding position, the holding device being connected to the storage unit in said second holding position, into a second release position, the holding device being released from the storage unit in said second release position, and
      the first handling direction and the second handling direction are linearly independent of one another.

2. Holding device as defined in claim 1, wherein the first connecting device and the second connecting device are actuatable independently of one another.

3. Holding device as defined in claim 1, wherein the first connecting device is designed in such a manner that a first releasing force is required to transfer the first connecting device from the first connecting position into the first release position.

4. Holding device as defined in claim 1, further comprising a first restoring device for transferring the first connecting device from the first release position into the first connecting position.

5. Holding device as defined in claim 1, wherein the second connecting device is designed in such a manner that a second releasing force is required to transfer the second connecting device from the second connecting position into the second release position.

6. Holding device as defined in claim 1, further comprising a second restoring device for transferring the second connecting device from the second release position into the second connecting position.

7. Holding device as defined in claim 5, wherein the first releasing force and the second releasing force differ from one another according to at least one of an amount and a direction.

8. Holding device as defined in claim 5, wherein the first releasing force and the second releasing force are linearly independent of one another.

9. Holding device as defined in claim 5, wherein the first releasing force is smaller than the second releasing force.

10. Holding device as defined in claim 1, wherein the holding device defines a holding axis predetermining at least one of a position and a location of the implant when the implant is connected to the holding device.

11. Holding device as defined in claim 10, wherein the holding axis and the second handling direction are parallel or essentially parallel to one another.

12. Holding device as defined in claim 1, wherein the first connecting device comprises at least one holding element designed to connect the implant to the holding device in the first connecting position of the first connecting device.

13. Holding device as defined in claim 12, wherein at least one holding element builds up a first restoring force for forming the first restoring device during transfer of the first connecting device from the first connecting position into the first release position, the first connecting device being transferable back into the first connecting position with said restoring force.

14. Holding device as defined in claim 12, wherein the at least one holding element limits an implant receptacle for accommodating the implant.

15. Holding device as defined in claim 14, wherein the implant receptacle has an undercut.

16. Holding device as defined in claim 1, wherein the indicating device comprises at least one indicating element adapted to be at least one of destroyed and plastically deformed during transfer of the first connecting device from the first connecting position into the first release position.

17. Holding device as defined in claim 1, wherein the at least one indicating element is formed by a holding element.

18. Holding device as defined in claim 1, wherein the holding device comprises a plate-like body.

19. Holding device as defined in claim 18, wherein the indicating element is designed in one piece with the body.

20. Holding device as defined in claim 1, further comprising a data storage device for storing implant data.

21. Holding device as defined in claim 1, wherein the second connecting device comprises at least one connecting element designed to connect the holding device to the storage unit in the second connecting position of the second connecting device.

22. Holding device as defined in claim 21, wherein:
for forming a snap-in connection the at least one connecting element comprises at least one snap-in element or is designed as a snap-in element, and
the snap-in element is in engagement or is adapted to be brought into engagement interlockingly with the storage unit in the second connecting position of the second connecting device.

23. Holding device as defined in claim 21, wherein the at least one connecting element is at least one of movable and deformable within a connecting plane.

24. Holding device as defined in claim 21, wherein the at least one connecting element limits an undercut area for accommodating a section of the storage unit in the second connecting position of the second connecting device.

25. Holding device as defined in claim 21, wherein the second connecting device comprises at least one essentially U-shaped material section having two legs of the U extending parallel or essentially parallel to a holding axis, said legs being connected to one another via a base of the U.

26. Holding device as defined in claim 1, wherein the second connecting device has at least one actuating element for transferring the second connecting device from the second connecting position into the second release position.

27. Holding device as defined in claim 1, further comprising at least one securing device preventing any implantation of the implant when the implant is connected to the holding device.

28. Holding device as defined in claim 1, further comprising a guiding device for positioning the holding device relative to the storage unit.

29. Holding device as defined in claim 1 with at least one implant.

30. Storage unit for accommodating and/or securing in place at least one holding device for an implant, comprising:
a plate having a plurality of receptacles each adapted to accept a holding device for an implant;
a frame surrounding the plate for spacing the plate from a mounting surface;
wherein the holding device comprises;
a first connecting device for releasably connecting the holding device and the implant, the first connecting device being transferable from a first connecting position, an implant being connectable or connected to the holding device in said first connecting position, into a first release position, the holding device releasing the implant in said first release position,
an indicating device indicating an at least one-time transfer of the first connecting device from the first connecting position into the first release position, and
a second connecting device for releasably connecting the holding device and a storage unit,
wherein:
the first connecting device is designed in such a manner that the implant is adapted to be handled in a first handling direction during movement from a first holding position, the implant being connected to the holding device in said first holding position, into the first release position,
the second connecting device is designed in such a manner that the holding device is adapted to be handled in a second handling direction during movement from a second holding position, the holding device being connected to the storage unit in said second holding position, into a second release position, the holding device being released from the storage unit in said second release position, and
the first handling direction and the second handling direction are linearly independent of one another.

31. Storage unit as defined in claim 30, wherein the first connecting device and the second connecting device are actuatable independently of one another.

* * * * *